(12) United States Patent
Umetsu et al.

(10) Patent No.: US 10,350,456 B2
(45) Date of Patent: Jul. 16, 2019

(54) EXERCISE CONTENT SETTING SYSTEM, EXERCISE CONTENT SETTING APPARATUS, EXERCISE CONTENT SETTING METHOD, AND EXERCISE CONTENT SETTING PROGRAM

(71) Applicant: Seiko Epson Corporation, Tokyo (JP)

(72) Inventors: Jun Umetsu, Chino (JP); Ryoma Shirouzu, Suwa-gun (JP); Hironori Hasei, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 182 days.

(21) Appl. No.: 15/271,059

(22) Filed: Sep. 20, 2016

(65) Prior Publication Data
US 2017/0100636 A1    Apr. 13, 2017

(30) Foreign Application Priority Data

Oct. 8, 2015 (JP) ................................. 2015-200513

(51) Int. Cl.
| | |
|---|---|
| A63B 24/00 | (2006.01) |
| G06F 19/00 | (2018.01) |
| G06Q 10/06 | (2012.01) |
| G09B 19/00 | (2006.01) |
| A61B 5/11 | (2006.01) |

(52) U.S. Cl.
CPC ............ *A63B 24/0075* (2013.01); *A61B 5/11* (2013.01); *A63B 24/0062* (2013.01); *G06F 19/3481* (2013.01); *G06Q 10/0639* (2013.01); *G09B 19/0038* (2013.01); *A63B 2220/62* (2013.01); *A63B 2230/75* (2013.01)

(58) Field of Classification Search
CPC ............ A63B 24/0062; A63B 24/0075; A63B 2220/00; A63B 2220/62; A63B 2220/75; A63B 2225/00; A63B 2225/20; A63B 2225/50; A61B 5/11; G06F 19/3481; G09B 19/00; G09B 19/0038
See application file for complete search history.

(56) References Cited

U.S. PATENT DOCUMENTS

| | | | | |
|---|---|---|---|---|
| 5,916,063 A * | 6/1999 | Alessandri | ............. | A63B 24/00 482/4 |
| 6,601,016 B1 * | 7/2003 | Brown | ............... | A63B 24/0062 702/182 |
| 6,702,719 B1 * | 3/2004 | Brown | .................. | A63B 22/00 482/8 |
| 7,722,503 B1 * | 5/2010 | Smith | ................ | A63B 24/0062 482/1 |

(Continued)

FOREIGN PATENT DOCUMENTS

| | | |
|---|---|---|
| JP | 2004-341619 A | 12/2004 |
| JP | 2005-205167 A | 8/2005 |

(Continued)

*Primary Examiner* — Milap Shah
(74) *Attorney, Agent, or Firm* — ALG Intellectual Property, LLC

(57) ABSTRACT

An exercise content setting system includes a terminal apparatus that acquires and transmits the daily activity information of a user; and an exercise content setting apparatus that sets exercise content information indicating content of an exercise according to a preset purpose based on the activity information acquired from the terminal apparatus.

17 Claims, 14 Drawing Sheets

(56) References Cited

U.S. PATENT DOCUMENTS

| | | | | |
|---|---|---|---|---|
| 8,719,202 B1* | 5/2014 | Maeng | G06N 99/005 | 706/45 |
| 9,283,429 B2 | 3/2016 | Aragones et al. | | |
| 9,618,527 B2* | 4/2017 | McGown | A63B 24/0062 | |
| 9,785,827 B1* | 10/2017 | Ray | G06K 9/00342 | |
| 9,913,590 B2* | 3/2018 | Kim | A61B 5/6895 | |
| 2001/0041647 A1* | 11/2001 | Itoh | A63B 22/00 | 482/9 |
| 2002/0019586 A1* | 2/2002 | Teller | A61B 5/02055 | 600/300 |
| 2002/0022551 A1* | 2/2002 | Watterson | H04L 67/02 | 482/8 |
| 2002/0147693 A1* | 10/2002 | Banerjee | G06Q 20/127 | 705/400 |
| 2002/0191035 A1* | 12/2002 | Selent | G06F 3/0481 | 715/866 |
| 2004/0033862 A1* | 2/2004 | Wu | A63B 22/02 | 482/8 |
| 2004/0077462 A1* | 4/2004 | Brown | A63B 24/0084 | 482/8 |
| 2004/0198554 A1* | 10/2004 | Orr | A63B 24/00 | 482/8 |
| 2005/0272564 A1* | 12/2005 | Pyles | A63B 22/0257 | 482/54 |
| 2006/0020174 A1 | 1/2006 | Matsumura et al. | | |
| 2006/0046898 A1* | 3/2006 | Harvey | A63B 71/0697 | 482/8 |
| 2006/0252602 A1* | 11/2006 | Brown | A63B 24/0084 | 482/9 |
| 2007/0082788 A1* | 4/2007 | Ciervo | A61B 5/0002 | 482/8 |
| 2007/0265138 A1* | 11/2007 | Ashby | G16H 20/30 | 482/8 |
| 2008/0090703 A1* | 4/2008 | Rosenberg | A63B 24/00 | 482/8 |
| 2008/0176713 A1* | 7/2008 | Olivera Brizzio | A63B 24/00 | 482/8 |
| 2010/0003652 A1* | 1/2010 | Lavie | G06Q 10/10 | 434/219 |
| 2010/0009810 A1* | 1/2010 | Trzecieski | A63B 24/0062 | 482/8 |
| 2013/0225370 A1* | 8/2013 | Flynt | A63B 24/0087 | 482/4 |
| 2015/0240507 A1* | 8/2015 | Kolodny | E04H 3/14 | 52/234 |
| 2015/0286799 A1* | 10/2015 | Padmani | G06F 19/00 | 705/3 |
| 2015/0360083 A1* | 12/2015 | Lagree | A63B 24/0075 | 482/130 |
| 2016/0129311 A1* | 5/2016 | Yang | A63B 24/0075 | 482/7 |
| 2018/0126222 A1* | 5/2018 | Duale | G06Q 10/02 | |

FOREIGN PATENT DOCUMENTS

| | | |
|---|---|---|
| JP | 2007-313280 A | 12/2007 |
| JP | 2009-112732 A | 5/2009 |
| JP | 2014-074976 A | 4/2014 |
| JP | 2015-501700 A | 1/2015 |
| WO | WO-2013-78208 A | 5/2013 |

* cited by examiner

| IDENTIFICATION INFORMATION | NAME | DATE OF BIRTH | AGE | SEX | HEIGHT | WEIGHT | PURPOSE | FAVORITE EQUIPMENT | DISLIKE EQUIPMENT |
|---|---|---|---|---|---|---|---|---|---|
| A01 | △KAWA△O | 1980.04.15 | 35 | MALE | 175 | 95 | DIET | CROSS TRAINER | — |
| A02 | ×TA×RO | 1973.12.09 | 41 | MALE | 170 | 65 | DIET | TREADMILL | POOL |
| A03 | OYAMAOMI | 1992.10.05 | 23 | FEMALE | 160 | 52 | IMPROVEMENT IN PHYSICAL STRENGTH | POOL | BENCH PRESS |
| ... | ... | ... | ... | ... | ... | ... | ... | ... | ... |

FIG. 8

| EQUIPMENT NAME | | 13:00 | 14:00 | 15:00 | 16:00 |
|---|---|---|---|---|---|
| TREADMILL | A | A11 | A18 | | |
| | B | A32 | | | |
| BIKE | A | A11 | A18 | A25 | A07 |
| | B | | | | |
| CROSS STRAINER | A | | A29 | A29 | |
| | B | | | | |
| CHEST PRESS | A | | A25 | | |
| | B | | A29 | A07 | |
| LEG PRESS | A | | | | |
| | B | | A32 | | |
| BENCH PRESS | A | | | A07 | A18 |
| | B | | | A11 | A32 |
| POOL | A | A25 | | | A38 |
| | B | | | | |

FIG. 9

EXERCISE CONTENT SETTING SYSTEM, EXERCISE CONTENT SETTING APPARATUS, EXERCISE CONTENT SETTING METHOD, AND EXERCISE CONTENT SETTING PROGRAM

CROSS-REFERENCES TO RELATED APPLICATIONS

This application claims priority to Japanese Patent Application No. 2015-200513, filed Oct. 8, 2015, the entirety of which is herein incorporated by reference.

BACKGROUND

1. Technical Field

The present invention relates to an exercise content setting system, an exercise content setting apparatus, an exercise content setting method, and an exercise content setting program.

2. Related Art

In the related art, personal training systems generating exercise programs personalized for users have been known (for example, see JP-T-2015-501700).

A kind of personal training system disclosed in JP-T-2015-501700 is configured to include an imaging device and a sensor that detect and measure an exercise action of a user, a display, and a computer such as a video game console.

In the personal training system, the computer generates an instruction of an exercise action which is supplied to a user (exerciser) and displays the instruction. Then, an image of the user performing an exercise action is acquired by the imaging device and data of the user performing the exercise action is measured by the sensor. Thereafter, the computer generates a personalized exercise program that generates human action screening scores for clarifying a region (a body part) which can be improved by an exercise based on the image acquired by the imaging device and the data measured by the sensor and includes a plurality of exercises started from other phases based on the human action screening scores, purposes, and the like of users. The exercise program is presented to the users.

However, in the personal training system disclosed in JP-T-2015-501700, the personalized exercise program based on the human action screening scores, purposes, and the like of the users is generated after the users perform instructed exercise actions. For this reason, there is a problem that, for example, it is necessary for users utilizing facilities of training gyms, fitness clubs, or the like to perform the exercise actions in the facilities.

In recent years, users having purposes of diets or an improvement in physical strengths and performing exercises in the facilities have increased. As the users, there are peoples who perform exercises daily as well as in facilities and people who perform exercises only in facilities and do not perform exercises daily. The users listen to counsels with trainers as necessary and decide exercise menus (training programs) of the users in many cases, but there is a problem that exercise situations in places other than facilities are not necessarily considered.

SUMMARY

An advantage of some aspects of the invention is that it provides an exercise content setting system, an exercise content setting apparatus, an exercise content setting method, and an exercise content setting program capable of setting exercise content appropriate for purposes of users simply.

An exercise content setting system according to a first aspect of the invention includes: a terminal apparatus that acquires and transmits daily activity information of a user; and an exercise content setting apparatus that sets exercise content information indicating an exercise content according to a preset purpose based on the activity information acquired from the terminal apparatus.

Information derived from a measurement result obtained by measuring an activity state of the user can be set as the activity information. As the terminal apparatus, not only a measurement apparatus which is mounted on the user and acquires the activity information but also a processing terminal which communicates with the measurement apparatus and is capable of acquiring and transmitting the activity information can be exemplified.

According to the first aspect of the invention, the exercise content information according to the preset purpose is set based on the daily activity information of the user. Thus, for example, in a case in which the exercise content setting apparatus is disposed in the facility, the user entering the facility can set the exercise content information without performing a predetermined exercise motion when the user enters the facility. Accordingly, it is possible to simply set the exercise content appropriate for the purpose of the user.

In the first aspect of the invention, it is preferable that the activity information includes at least one of an exercise intensity of the exercise performed by the user, an exercise time of the exercise, consumed calories of the user, a calorie balance which is a balance of intake calories and the consumed calories of the user, an index value regarding a sleep state of the user, and an index value regarding a degree of fatigue of the user.

As the exercise intensity, an exercise intensity based on a maximum oxygen intake amount or an exercise intensity based on a pulse rate or a heart rate by the Karvonen formula or the like can be exemplified.

Here, by determining the exercise intensity and the exercise time of the exercise performed by the user or the consumed calories of the user, it is possible to ascertain the load of the exercise performed by the user. By determining the calorie balance of the user, it is possible to ascertain an effort state of diet in a case in which the purpose is the diet. Further, by determining the index value regarding the sleep state of the user and the index value regarding the degree of fatigue, it is possible to ascertain the physical body state of the user.

Therefore, by including at least one of the foregoing items in the activity information, it is possible to appropriately ascertain the user state. Accordingly, it is possible to simply and appropriately set the exercise content information according to the activity state and the purpose of the user.

In the first aspect of the invention, it is preferable that the exercise content setting apparatus transmits the set exercise content information to the terminal apparatus.

In such a configuration, when the terminal apparatus includes the report unit such as a display unit, the terminal apparatus receives and reports the exercise content information, and thus the user can easily ascertain the exercise content information.

In the first aspect of the invention, it is preferable that the exercise content setting apparatus includes an information accumulation apparatus that accumulates the activity information and an information processing apparatus that acquires the activity information from the information accumulation apparatus and sets the exercise content information based on the acquired activity information.

The information accumulation apparatus and the information processing apparatus may be separated or integrated.

In such a configuration, the information accumulation apparatus accumulates the activity information acquired with the terminal apparatus, and thus it is possible to reduce the storage capacity for storing the activity information in the terminal apparatus.

In a case in which the information accumulation apparatus and the information processing apparatus are configured to be separated, it is possible to reduce each processing load and it is also possible to dispose the information accumulation apparatus and the information processing apparatus at mutually distant positions.

Conversely, when the information accumulation apparatus and the information processing apparatus are integrated, occurrence of a time lag is suppressed in the acquisition of the activity information by the information processing apparatus. Therefore, it is possible to suppress delay of the process of setting the exercise content information by the information processing apparatus.

In the first aspect of the invention, it is preferable that the exercise content information includes at least one of an exercise intensity and an exercise time of the exercise performed by the user and an exercise menu set based on the exercise intensity and the exercise time.

In such a configuration, in a case in which the exercise intensity and the exercise time are included in the exercise content information, the load of the exercise to be performed can be ascertained based on the exercise intensity and the exercise time. Therefore, by performing the exercise according to the exercise content information, it is possible to reliably perform the exercise appropriate for the purpose. On the other hand, in a case in which the exercise menu is included in the exercise content information, even the user who has no sufficient knowledge about the exercise intensity or the like can reliably and simply perform the exercise appropriate for the purpose by performing the exercise according to the exercise menu.

In the first aspect of the invention, it is preferable that the exercise content setting apparatus retains use information indicating a use state of equipment disposed in a facility, and in a case in which the exercise menu is included in the exercise content information, the exercise menu in which a waiting time is shortest is set based on the use information when the user uses the equipment.

In this case, the exercise content setting apparatus is preferably disposed in a facility such as a training gym or a fitness club.

In such a configuration, in a case in which the user enters the facility and performs an exercise indicated by the exercise menu using at least one piece of equipment, the user can perform the exercise efficiently in a shortest waiting time and can also utilize the equipment in the facility efficiently.

In the first aspect of the invention, it is preferable that the exercise content setting system further include a result information generation apparatus that generates exercise result information indicating a result of the exercise performed by the user according to the exercise content information.

The result information generation apparatus may be separated from or integrated with the exercise content setting apparatus.

In such a configuration, the user can easily ascertain the content of the exercise performed by the user by confirming the exercise result information. Accordingly, it is possible to further improve a motivation of the exercise.

In the first aspect of the invention, it is preferable that content of the exercise indicated by the exercise content information is content of an exercise performed in a predetermined facility, and the exercise content setting system further includes an additional exercise setting apparatus that sets additional information indicating an exercise content to be performed by the user outside the predetermined facility according to the purpose based on a result of the exercise performed by the user according to the exercise content information.

The additional exercise setting apparatus may be separated from or integrated with the exercise content setting apparatus.

In such a configuration, not only the content of the exercise to be performed by the user in the predetermine facility but also the additional information indicating the content of the exercise to be performed outside the facility are generated as tasks. Thus, since the exercise content information and the additional information are presented to the user for implementation, the user can be easily accustomed to have the exercise habit. Further, the user can perform the exercise appropriate for the purpose not only in the facility but also outside the facility when the user performs the exercise according to the additional information.

In the first aspect of the invention, it is preferable that content of the exercise indicated by the exercise content information is content of an exercise performed in a predetermined facility, and the exercise content setting apparatus sets the exercise content information according to a scheduled stay time of the user in the predetermined facility.

In such a configuration, even the user whose scheduled stay time is short can efficiently perform the exercise appropriate for the purpose.

In the first aspect of the invention, it is preferable that the terminal apparatus retains unique identification information, and exercise content setting apparatus acquires the identification information and specifies the user based on the acquired identification information.

In such a configuration, for example, the terminal apparatus used by the user can be used instead of a membership card of the training gym or the like. Accordingly, it is possible to improve versatility and convenience of the terminal apparatus.

In the first aspect of the invention, it is preferable that the exercise content setting apparatus sets the exercise content information based on an exercise time of the user based on the activity information and a within-range exercise time which is a time in which the exercise is performed within a predetermined exercise intensity range in the exercise time.

Here, in a case in which the purpose is, for example, a diet or an improvement in the body strength and a case in which an implementation time of the exercise is relatively short within an exercise intensity range in which fat burning or muscle strengthening is efficiently performed, it may be difficult to say that the exercise appropriate for the purpose is sufficiently performed although the daily exercise time is relatively long.

In such a configuration, since the exercise content information is set in consideration of the daily exercise time and the within-range exercise time, a load of the exercise to be performed by the user can be adjusted, for example, in a case in which the exercise appropriate for the purpose is not sufficiently performed or a case in which the physical and mental states are determined to be in a fatigue state due to a considerably large load. Accordingly, it is possible to perform the exercise appropriate for the user state.

An exercise content setting apparatus according to a second aspect of the invention includes: an activity information acquisition unit that acquires daily activity information of a user; and an exercise content setting unit that sets an exercise content according to a preset purpose based on the acquired activity information.

According to the second aspect of the invention, it is possible to obtain the same advantages as those of the exercise content setting system according to the first aspect of the invention.

An exercise content setting method according to a third aspect of the invention is adopted using an information processing apparatus and is a method of setting an exercise content performed by a user. The method includes: acquiring daily activity information of the user by the information processing apparatus; and setting an exercise content according to a preset purpose based on the acquired activity information by the information processing apparatus.

As the information processing apparatus, a computer such as a personal computer (PC) or a server can be exemplified.

According to the third aspect of the invention, it is possible to obtain the same advantages as those of the exercise content setting apparatus according to the second aspect of the invention by adopting the exercise content setting method using the information processing apparatus.

An exercise content setting program according to a fourth aspect of the invention is executed by an information processing apparatus and sets an exercise content performed by a user. The program causes the information processing apparatus to perform: acquiring daily activity information of the user; and setting an exercise content according to a preset purpose based on the acquired activity information.

According to the fourth aspect of the invention, the information processing apparatus can obtain the same advantages as those of the exercise content setting apparatus according to the second aspect of the invention when the information processing apparatus executes the exercise content setting program.

The exercise content setting program may be recorded on a recording medium so that the exercise content setting program can be read by a computer. The information processing apparatus can obtain the same advantages as those of the exercise content setting apparatus according to the second aspect of the invention when the information processing apparatus reads the exercise content setting program from the recording medium and executes the exercise content setting program. As the recording medium, a magnetic tape, a magnetic disk, an optical disc, a magneto-optical disc, a hard disk drive (HDD), and a semiconductor memory can be exemplified. The exercising content setting program can be executed in the information processing apparatus using such a recording medium. Additionally, the exercise presentation program may be supplied via a network.

BRIEF DESCRIPTION OF THE DRAWINGS

The invention will be described with reference to the accompanying drawings, wherein like numbers reference like elements.

FIG. 8 is a diagram illustrating content of a user table according to the embodiment.

FIG. 9 is a diagram illustrating content of a use situation table according to the embodiment.

DESCRIPTION OF EXEMPLARY EMBODIMENTS

Hereinafter, an embodiment of the invention will be described with reference to the drawings.

Schematic Configuration of Exercise Content Setting System

Figure 1:
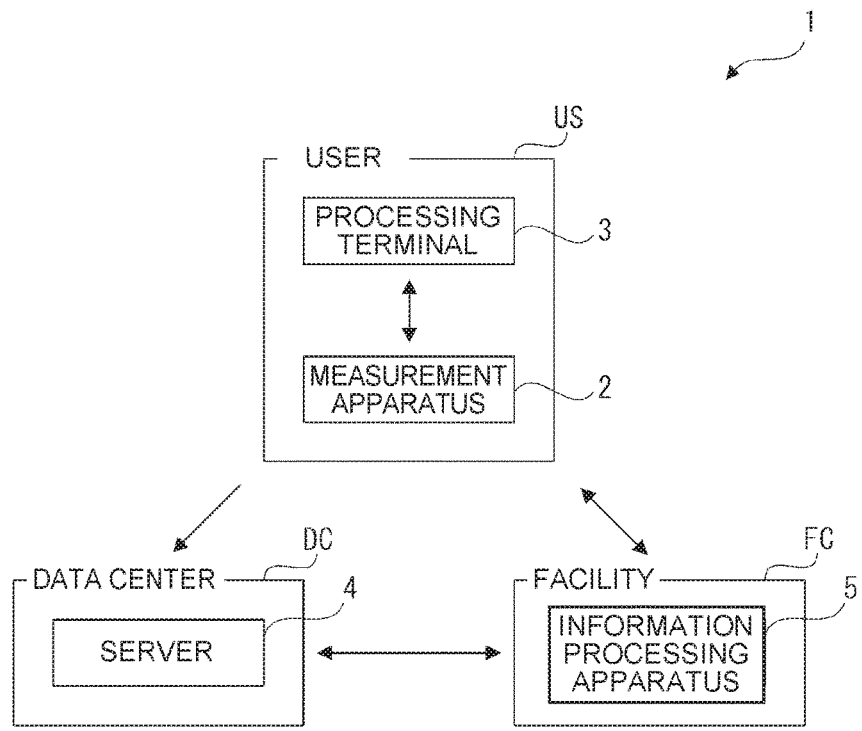
FIG. 1 is a schematic diagram illustrating the configuration of an exercise content setting system according to an embodiment of the invention.

FIG. 1 is a schematic diagram illustrating the configuration of an exercise content setting system 1 according to the embodiment.

The exercise content setting system 1 according to the embodiment is configured to include a measurement apparatus 2 and a processing terminal 3 used by a user US, a server 4, and an information processing apparatus 5, as illustrated in FIG. 1. Of the apparatuses, the measurement apparatus 2 and the processing terminal 3 correspond to a terminal apparatus according to the invention, and the server 4 and the information processing apparatus 5 form an exercise content setting apparatus according to the invention.

In the exercise content setting system 1, the information processing apparatus 5 is installed in, for example, a facility FC such as a training gym and the measurement apparatus 2 which also functions as a membership card used for authenticate the user US is lent to the user US when the user US enters the facility FC. A daily activity state (exercise state) of the user US is measured by the measurement apparatus 2 and activity information indicating the activity state is collected and accumulated from the measurement apparatus 2 or the processing terminal 3 communicating with the measurement apparatus 2 by the server 4 located on a network such as the Internet. Further, when the user US enters the facility FC, the information processing apparatus 5 authenticating the user US acquires the activity information indicating daily activity state of the authenticated user US from the server 4, and the information processing apparatus 5 sets and supplies exercise content information which is appropriate for the purpose of the user US and includes not only an exercise intensity (recommended exercise intensity) and an exercise time (recommended exercise time) based on the activity information but also an exercise menu (training menu) in the facility FC. In this way, the exercise content setting system 1 has one feature in that the exercise content information indicating the content of an exercise appropriate for the user is simply set and supplied.

The configuration of the exercise content setting system 1 will be described below.

Configuration of Measurement Apparatus

Figure 2:
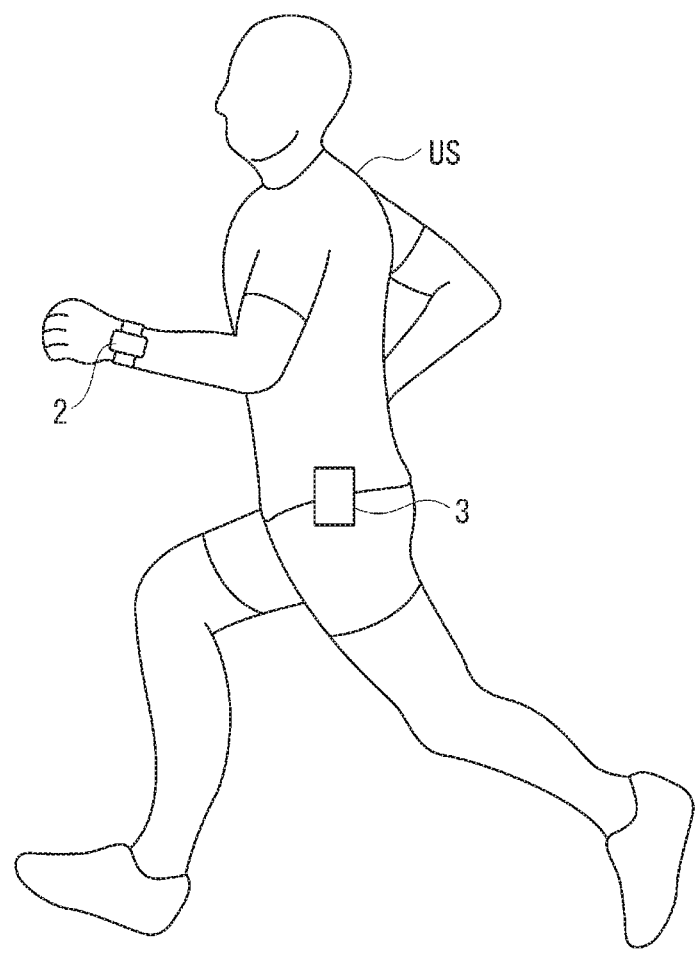
FIG. 2 is a diagram illustrating an example of a use state of a measurement apparatus according to the embodiment.
Figure 3:
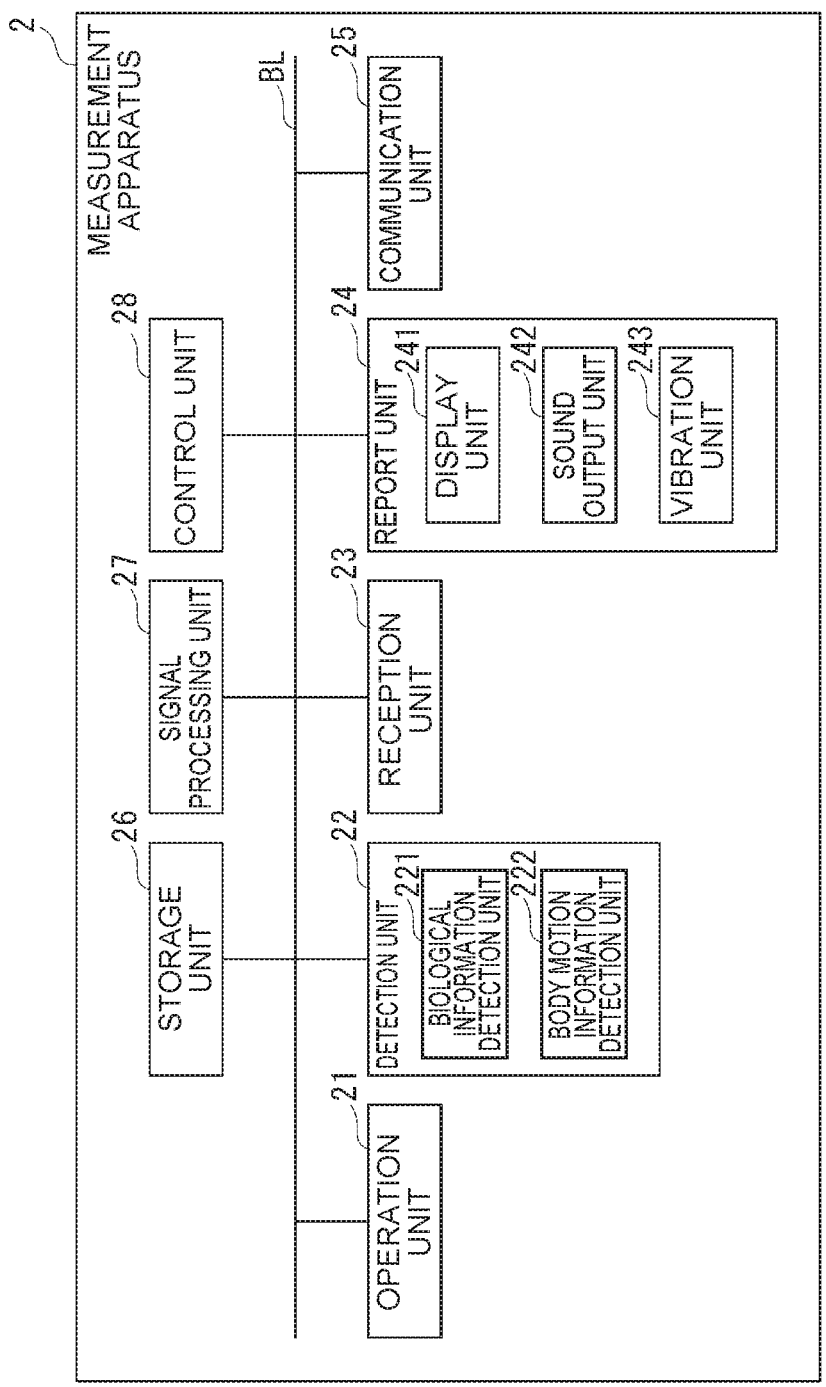
FIG. 3 is a block diagram illustrating the configuration of the measurement apparatus according to the embodiment.

FIG. 2 is a diagram illustrating an example of a use state of the measurement apparatus 2. FIG. 3 is a block diagram illustrating the configuration of the measurement apparatus 2.

As illustrated in FIG. 2, the measurement apparatus 2 is a wearable apparatus used for the user US. The measurement apparatus 2 is mounted on a part (a wrist in the example of FIG. 2) of the body of the user US, detects and measures biological information and body motion information of the user US, and measures positional information.

As illustrated in FIG. 3, the measurement apparatus 2 includes an operation unit 21, a detection unit 22, a reception unit 23, a report unit 24, a communication unit 25, a storage unit 26, a signal processing unit 27, and a control unit 28. The units 21 to 28 are connected to each other via a bus line BL.

Configuration of Operation Unit

The operation unit 21 includes a plurality of buttons disposed on an exterior case of the measurement apparatus 2 and outputs an operation signal according to an input (pressed) button to the control unit 28. The operation unit 21 detects a tapping operation of the user and outputs an operation signal according to the tapping operation to the control unit 28. The operation unit 21 further includes a touch panel disposed on a display unit 241 to be described below and outputs an operation signal according to an operation of the user on the touch panel to the control unit 28. The invention is not limited to the configuration. The configuration of the operation unit 21 does not matter as long as an operation signal according to an operation of the user can be output to the control unit 28.

For example, meal information regarding intake meals of the user can be input through an input operation on the operation unit 21. The meal information is information that includes intake dates of the meals of the user and content of the meals. As the content of the meals, items of the intake meals or intake calories based on the items can be exemplified. The meal information may be configured to be input with the processing terminal 3 to be described below.

Configuration of Detection Unit

The detection unit 22 includes a biological information detection unit 221 and a body motion information detection unit 222 that detect biological information and body motion information of the user, respectively, and outputs detection results of the units to the control unit 28.

In the embodiment, the biological information detection unit 221 detects pulse waves as biological information and outputs a pulse wave signal indicating the pulse waves. The invention is not limited thereto. The biological information detection unit 221 may be configured to detect another biological information such as brain waves, electrocardiogram, body temperature, or a sweat rate, instead of or in addition to the pulse waves.

The body motion information detection unit 222 detects acceleration varying according to a body motion of the user as the body motion information of the user and outputs an acceleration signal indicating a variation in the acceleration. The body motion information detection unit 222 can be configured to include, for example, an acceleration sensor of orthogonal three axes. The invention is not limited to thereto and the body motion information detection unit 222 may be configured to include a gyro sensor.

Configuration of Reception Unit

The reception unit 23 acquires positional information indicating a current position of the measurement apparatus 2 (positional information indicating a current position of the user). The reception unit 23 can be configured to include a module that acquires the positional information based on radio waves received from satellites in correspondence to a satellite positioning system such as the global positioning system (GPS). The reception unit 23 can also be configured to calculate the positional information using communication wireless radio waves.

The reception unit 23 acquires the positional information for each predetermined time. However, the positional information may be configured to be acquired only while an analysis unit 286 to be described below determines that the user is doing an exercise. The reception unit 23 may be configured to receive a signal for calculating the positional information, perform digital conversion, and output the converted signal to the signal processing unit 27, so that the positional information can be calculated in the signal processing unit 27.

Configuration of Report Unit

The report unit 24 reports various kinds of information under the control of the control unit 28. The report unit 24 reports, for example, an operation state of the measurement apparatus 2 or the acquired biological information, body motion information, or positional information. Additionally, the report unit 24 reports various kinds of information acquired from the processing terminal 3, the server 4, and the information processing apparatus 5. The report unit 24 includes a display unit 241, a sound output unit 242, and a vibration unit 243.

The display unit 241 includes a liquid crystal display or an electro-luminescence (EL) display and displays an image according to an image signal input from the control unit 28.

The sound output unit 242 includes a sound output unit such as a speaker and outputs a sound according to sound information input from the control unit 28.

The vibration unit 243 includes a motor of which driving is controlled by the control unit 28 and reports the information by vibration generated through the driving of the motor.

Configuration of Communication Unit

The communication unit 25 has a communication module capable of communicating with an external apparatus such as the processing terminal 3, the server 4, and the information processing apparatus 5 directly or via a network. For example, the communication unit 25 transmits the acquired biological information, body motion information, or positional information to the external apparatus under the control of the control unit 28. The communication unit 25 transmits a pulse rate and a pace (pitch) calculated based on the biological information and the body motion information, or an exercise intensity and an exercise time. Further, the communication unit 25 transmits activity information generated by the control unit 28 to the external device.

The communication unit 25 has a communication module configured to be able to communicate with an external apparatus present relatively nearby, for example, by a communication scheme according to a short-range wireless communication standard such as IEEE 802.15. Additionally, the communication unit 25 has a communication module configured to be able to communicate with an external apparatus located on a network such as the Internet using a public communication network, for example, by a communication scheme according to a communication standard such as IEEE 802.16 or Long Term Evolution (LTE).
Configuration of Storage Unit The storage unit 26 is configured to include a nonvolatile semiconductor memory such as a flash memory and stores a program or data necessary for an operation of the measurement apparatus 2. For example, the storage unit 26 stores the acquired biological information and body motion information of the user or the measured positional information. The storage unit 26 stores the input meal information and additionally stores analysis result information obtained by analyzing the biological information and the body motion information by the control unit 28 to be described below. The analysis result information will be described in detail below.

Further, the storage unit 26 stores identification information unique to the measurement apparatus 2. The identification information is acquired by the information processing apparatus 5 to be described below and is used to authenticate the user. The identification information may be acquired from the information processing apparatus 5 and may be stored in the storage unit 26.
Configuration of Signal Processing Unit The signal processing unit 27 has a signal processing circuit such as a digital signal processor (DSP) and performs signal processing on pulse wave signals which are biological information detected by the detection unit 22 and an acceleration signal which is body motion information detected by the detection unit 22.

For example, the signal processing unit 27 obtains a pulsation signal by removing a body motion noise component based on the acceleration signal detected by the body motion information detection unit 222 from the pulse wave signal detected by the biological information detection unit 221. The signal processing unit 27 performs frequency analysis, such as Fast Fourier transform (FFT), on the pulsation signal and the acceleration signal and outputs an obtained process result (power spectrum) to the control unit 28.
Configuration of Control Unit FIG. 4 is a block diagram illustrating the configuration of the control unit 28.

The control unit 28 includes an arithmetic processing circuit such as a central processing unit (CPU) and controls an operation of the measurement apparatus 2 autonomously or according to an operation signal input from the operation unit 21 according to an operation of the user. For example, the control unit 28 analyzes a process result by the signal processing unit 27 and additionally transmits various kinds of information to the information processing apparatus 5 via the communication unit 25.

Figure 4:
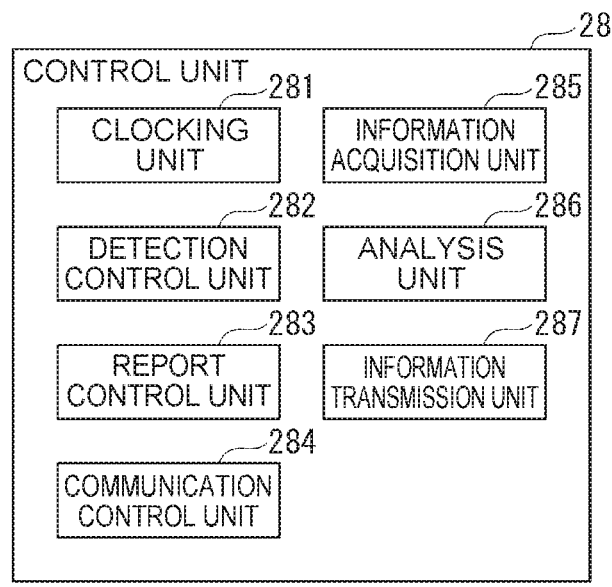
FIG. 4 is a block diagram illustrating the configuration of a control unit of the measurement apparatus according to the embodiment.

As illustrated in FIG. 4, the control unit 28 includes a clocking unit 281, a detection control unit 282, a report control unit 283, a communication control unit 284, an information acquisition unit 285, an analysis unit 286, and an information transmission unit 287 realized when the arithmetic processing circuit executes a program stored in the storage unit 26.

The clocking unit 281 clocks a current date.

The detection control unit 282 controls an operation of the detection unit 22.

The report control unit 283 controls an operation of the report unit 24. For example, the report control unit 283 outputs report information indicating an operation state of the measurement apparatus 2, a detection result by the detection unit 22, an analysis result by the analysis unit 286, and various kinds of information acquired by the communication unit 25 to the report unit 24 and reports the report information to the report unit 24.

The communication control unit 284 controls an operation of the communication unit 25.

The information acquisition unit 285 acquires various signals and various kinds of information input from the operation unit 21, the detection unit 22, the reception unit 23, the communication unit 25, and the signal processing unit 27. For example, the information acquisition unit 285 acquires the biological information and the body motion information input from the detection unit 22, the positional information input from the reception unit 23, a process result of the frequency analysis input from the signal processing unit 27, and the meal information. The information acquisition unit 285 stores such information in the storage unit 26 in association with date information indicating a current date clocked by the clocking unit 281.

The information acquisition unit 285 acquires the exercise content information indicating content of an exercise to be performed in the facility from the information processing apparatus 5 to be described below via the communication unit 25 and reports the exercise content information to the report unit 24 (for example, the display unit 241). The exercise content information will be described in detail below.

The analysis unit 286 calculates a pulse rate and the pace of the user by specifying the frequency of pulses and a body motion from the process result of the frequency analysis by the signal processing unit 27 and multiplying the frequency by a predetermined multiple (for example, 60 times). The pulse rate and the pace are analyzed by the analysis unit 286 for each predetermined time (for example, every 5 seconds).

The analysis unit 286 considers a time of a state in which the calculated pulse rate exceeds a first threshold value which is a predetermined pulse rate and the calculated pace exceeds a predetermined value as an exercise time in which the user performs an exercise and calculates the exercise time. Further, the analysis unit 286 calculates a time of a state in which the pulse rate exceeds a second threshold value greater than the first threshold value among the exercise times as a within-range exercise time (an exercise time within a zone). The first threshold value and the predetermined value are values set according to the pulse rate and the pace recorded when the user performs an exercise. The second threshold value is a value set according to the pulse rate when the user performs an exercise in which fat is efficiently consumed and an exercise appropriate for an increase in a muscle mass. A range exceeding the second threshold value is referred to as a zone.

Further, the analysis unit 286 calculates an exercise intensity in a period determined as an exercise time. The exercise intensity can be set as an exercise intensity calculated in accordance with, for example, the Karvonen formula, but may be an exercise intensity calculated in accordance with another method.

The analysis unit 286 stores such a calculation result in the storage unit 26.

The information transmission unit 287 transmits various kinds of information stored in the storage unit 26 to the processing terminal 3 or the server 4 via the communication unit 25.

Specifically, the information transmission unit 287 transmits analysis result information which is an analysis result by the analysis unit 286, identification information of the measurement apparatus 2, and daily activity information of the user including the meal information. Of the information, the analysis result information is, for example, information that includes an exercise time and the within-range exercise time of detection dates of a transition of each of the pulse rate and the pace and a transition of the acquired positional information, derivation information including a transition of the exercise intensity in the exercise time and the within-range exercise time, and date information indicating acquisition dates of the biological information, the body motion information, and the positional information serving as bases of the derivation information.

In a case in which the activity information is transmitted, the information transmission unit 287 transmits the identification information and information accumulated after the previous activity information to the processing terminal 3 or the server 4 in order to shorten a transmission time of the activity information. Therefore, a date in which the activity information is transmitted is stored in the storage unit 26. However, the invention is not limited thereto. The information transmission unit 287 may transmit the activity information including all of the analysis result information stored in the storage unit 26.

The information transmission unit 287 is configured to transmit the activity information in a case in which an operation signal according to an input operation of transmitting the activity information is input from the operation unit 21, a case in which request information requesting the activity information is received via the communication unit 25, a case in which the current time comes to a pre-decided transmission time, or a case in which a predetermined time passes after previous transmission.

As described above, in the case in which the processing terminal 3 sets the meal information and transmits the meal information to the server 4, the meal information may not included in the activity information transmitted to the processing terminal 3 or the server 4 by the measurement apparatus 2.

The analysis result information may include another derivation information derived based on various kinds of information acquired by the measurement apparatus 2. Examples of the other derivation information include intake calories, consumed calories, a calorie balance which is a balance of the intake calories and the consumed calories, a sleep index value regarding the quality and depth of sleep, an index value regarding the degree of fatigue, a running distance, and the number of steps. The analysis unit 286 analyzes the acquired various kinds of information to acquire the derivation information. For example, the intake calories can be acquired based on the meal information and the consumed calories can be acquired based on the biological information such as the pulse rate or the body motion information. The index value regarding the quality and depth of sleep and the index value regarding the degree of fatigue can be acquired based on the same biological information and body motion information. The running distance and the number of steps can be acquired based on the body motion information.

In a case in which request information requesting the identification information of the measurement apparatus 2 is received from the information processing apparatus 5 via the communication unit 25, the information transmission unit 287 transmits the identification information stored in the storage unit 26 to the information processing apparatus 5 which is a transmission source of the request signal.

After the user is authenticated based on the identification information by the information processing apparatus 5, the information transmission unit 287 transmits the activity information to the information processing apparatus 5 based on the request information from the information processing apparatus 5 while the user stays in the facility FC.

In the embodiment, the activity information can directly be transmitted from the measurement apparatus 2 to the server 4. Therefore, the activity information may not necessarily be transmitted to the server 4 via the processing terminal 3. However, the measurement apparatus 2 may be configured not to transmit the activity information to the server 4 and to transmit the activity information to the processing terminal 3 and the processing terminal 3 may be configured to transmit the activity information to the server 4. The activity information (the activation information in the facility) while the user stays in the facility FC may be transmitted from the measurement apparatus 2 to the server 4 via the information processing apparatus 5.

On the other hand, the measurement apparatus 2 may transmit the detection result by the detection unit 22, the acquisition result by the reception unit 23, and the acquisition dates of the results to the processing terminal 3, and the processing terminal 3 may generate the activity information based on the received information and transmit the activity information to the server 4. In this case, the measurement apparatus 2 may not include the analysis unit 286. The information transmitted from the measurement apparatus 2 and the processing terminal 3 may not include the positional information and the reception unit 23 may not be provided.

Configuration of Processing Terminal

Figure 5:
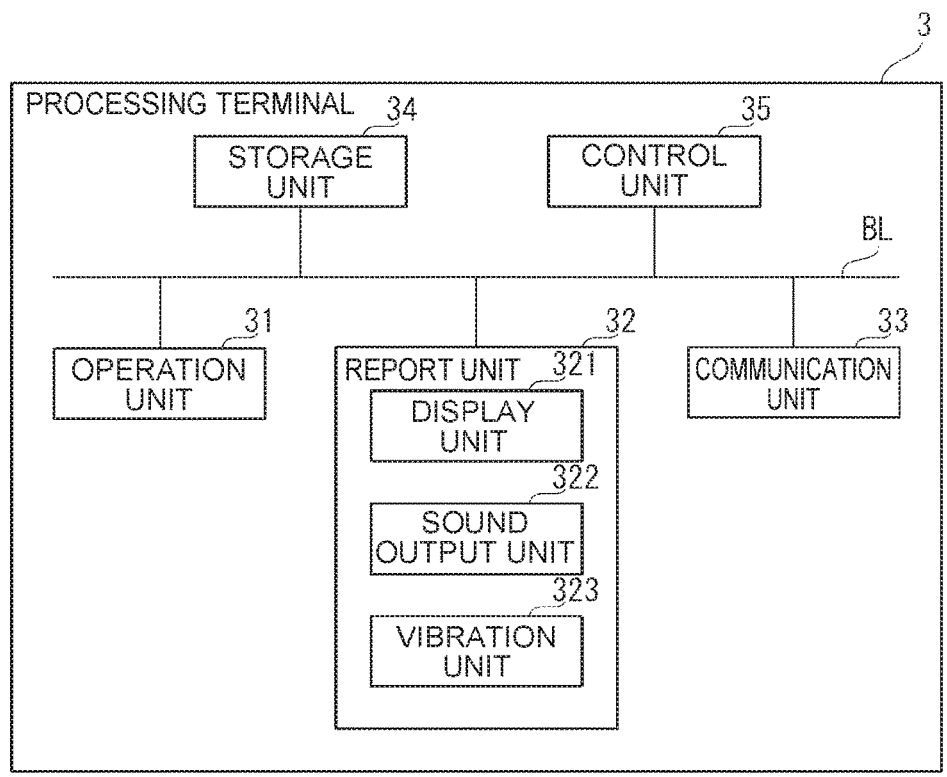
FIG. 5 is a block diagram illustrating the configuration of a processing terminal according to the embodiment.

FIG. 5 is a block diagram illustrating the configuration of the processing terminal 3.

As illustrated in FIG. 1, the processing terminal 3 is one of the terminal apparatuses of the invention and is an information terminal apparatus (computer) used by the user. Specifically, the processing terminal 3 can be configured to include a smartphone (multifunctional mobile phone), a tablet, a PC, or the like. In the embodiment, the processing terminal 3 is configured to include a smartphone, as illustrated in FIG. 3.

The processing terminal 3 communicates with the measurement apparatus 2 to acquire, store, and manages not only the biological information and the body motion information from the measurement apparatus 2 but also the activity information. Additionally, in a case in which the measurement apparatus 2 may not directly transmit the activity information to the server 4, the processing terminal 3 transmits the activity information received from the measurement apparatus 2 or the activity information generated by the processing terminal 3 to the server 4.

Figure 6:
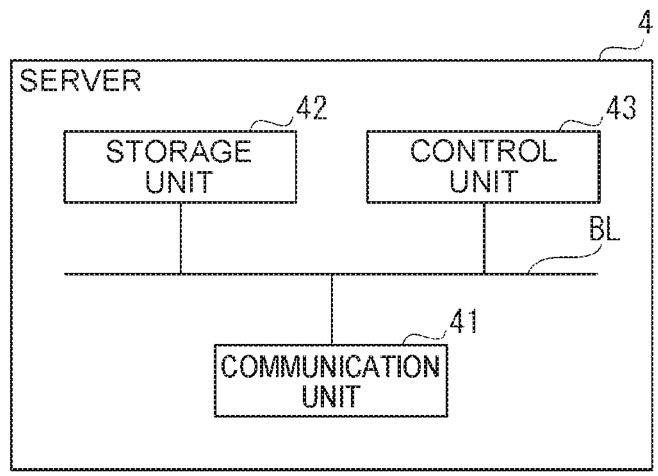
FIG. 6 is a block diagram illustrating the configuration of a server according to the embodiment.

As illustrated in FIG. 6, the processing terminal 3 includes an operation unit 31, a report unit 32, a communication unit 33, a storage unit 34, and a control unit 35. The units 31 to 35 are electrically connected to each other via the bus line BL.

Configuration of Operation Unit

As in the operation unit 21, the operation unit 31 receives an input operation by the user and outputs an operation signal according to the input operation to the control unit 35. For example, the operation unit 31 can be configured to include a touch panel or a physical key provided on the casing of the processing terminal 3 and can also be configured to include a keyboard and a pointing device connected to the processing terminal 3.

By operating the operation unit 31, it is possible to input the meal information.

Configuration of Report Unit

The report unit 32 reports various kinds of information to the user under the control of the control unit 35. As in the report unit 24, the report unit 32 includes a display unit 321, a voice output unit 322, and a vibration unit 323.

The display unit 321 includes any of various display panels such as a liquid crystal display panel and an organic EL display panel and displays a predetermined image under the control of the control unit 35 to be described below. Examples of the image include an image including the exercise content information received from the information processing apparatus 5 to be described below, an image including an exercise result, and an image including tasks up to a subsequent task.

The sound output unit 322 is configured to include a sound output unit such as a speaker and outputs a sound according to sound information input from the control unit 35.

The vibration unit 323 includes a motor that is driven under the control of the control unit 28 and generates vibration. In the embodiment, the processing terminal 3 is configured to include a smartphone, as described above, and thus the report unit 32 includes the vibration unit 323. In a case in which the processing terminal 3 is configured to include a tablet or a PC, the vibration unit may not be provided.

Configuration of Communication Unit

The communication unit 33 includes a communication module capable of communicating with the measurement apparatus 2, the server 4, and the information processing apparatus 5. Here, in a case in which the communication unit 33 communicates with the measurement apparatus 2, the server 4, and the information processing apparatus 5 in conformity to the same communication scheme, the communication unit 33 includes one communication module. Conversely, in a case in which at least one of a communication scheme at the time of communication with the measurement apparatus 2, a communication scheme at the time of communication with the server 4, and a communication scheme at the time of communication with the information processing apparatus 5 is different, the communication unit 33 includes a plurality of communication modules capable of performing communication in conformity to each of the communication schemes.

Configuration of Storage Unit

The storage unit 34 is configured to include a hard disk drive (HDD), a solid state drive (SSD), and a flash memory and stores various programs and data necessary for an operation of the processing terminal 3.

For example, the storage unit 34 stores connection information for communication connection with the measurement apparatus 2 as the data. The storage unit 34 stores information such as the activity information received from the measurement apparatus 2 by the communication unit 33.

On the other hand, the storage unit 34 stores, for example, an operating system (OS) or a management program managing the activity information received from the measurement apparatus 2 via the communication unit 33 as the program. The management program stores the biological information (pulse rate), the body motion information (pace), the positional information, and the exercise time (including the within-range exercise time) included in the same activity information for each detection date and each detection time based on the date information included in the received activity information, and manages the pieces of information. As described above, the activity information does not necessarily include the exercise time. Therefore, in a case in which the management program does not include the exercise time, the management program includes a program to calculate the exercise time. Further, in a case in which the activity information includes a detection signal by the detection unit 22, a program realizing a function of the signal processing unit 27 by software or a program realizing a function of the analysis unit 286 are also included in the management program. Furthermore, the management program may include a program that calculates intake calories of the user from input or selected items.

Configuration of Control Unit

The control unit 35 includes an arithmetic processing circuit such as a CPU and controls an operation of the processing terminal 3 autonomously or according to an operation signal input from the operation unit 31 according to an operation of the user by executing the OS stored in the storage unit 34.

The control unit 35 executes the management program and manages the activity information received and acquired from the measurement apparatus 2 with which communication is established based on the connection information. At this time, the control unit 35 calculates the pulse rate and the pace from the acquired biological information and body motion information, as necessary, and further calculates the exercise time and the within-range exercise time from the pulse rate, the pace, and the detection time, as necessary. Based on the activity information received and acquired from the measurement apparatus 2, the control unit 35 may derive the derivation information not included in the activity information. For example, in a case in which any one piece of derivation information is not included in the activity information transmitted from the measurement apparatus 2, the control unit 35 may be configured to derive the derivation information not included in the activity information or another derivation information.

In a case in which the measurement apparatus 2 may not directly communicate with the server 4, the control unit 35 transmits the activity information generated based on information acquired from the measurement apparatus 2 to the server 4 via the communication unit 33. At this time, in a case in which the meal information is input with the processing terminal 3 or a case in which the derivation information is derived, the control unit 35 includes the input meal information and the derived derivation information in the activity information and transmits the information to the server 4.

Configuration of Server

FIG. 6 is a block diagram illustrating the configuration of the server 4.

As illustrated in FIG. 1, the server 4 corresponds to an information accumulation apparatus included in the exercise content setting apparatus according to the invention and is disposed in, for example, a data center DC different from the facility FC in which the information processing apparatus 5 to be described below is disposed.

The server 4 communicates with at least one information transmission apparatus among the measurement apparatus 2 and the processing terminal 3, and receives and stores the activity information transmitted from the information transmission apparatus.

As illustrated in FIG. 6, the server 4 includes a communication unit 41, a storage unit 42, and a control unit 43. These units are connected to each other via a bus line BL. The server 4 may include an operation unit such as a keyboard or a pointing device and a display unit that displays an operation screen in addition to these units.

The communication unit 41 transmits and receives information with, for example, an external apparatus such as the measurement apparatus 2, the processing terminal 3, and the information processing apparatus 5 under the control of the control unit 43.

The storage unit 42 stores not only an OS necessary for an operation of the server 4 or various programs but also the activity information for each piece of identification information of the measurement apparatus 2.

The control unit 43 includes an arithmetic processing circuit such as a CPU and controls an operation of the server 4 by executing a program stored in the storage unit 42 by the arithmetic processing circuit, as in the control units 28 and 35. The control unit 43 stores, for example, the activity information received from the information transmission apparatus (at least one of the measurement apparatus 2 and the processing terminal 3) via the communication unit 41 in the storage unit 42.

In a case in which request information requesting activity information is received from the information processing apparatus 5 by the communication unit 41, the control unit 43 transmits the identification information included in the request information and the activity information according to acquisition period information included in the request information, as necessary. For example, in a case in which the identification information of the measurement apparatus 2 used by a certain user and the request information including the acquisition period information indicating a period from 18:00, Oct. 2, 2015 to 15:00 Oct. 9, 2015 are received, the control unit 43 generates transmission information including the activity information within the period among the pieces of activity information stored in the storage unit 42 in association with the identification information and transmits the transmission information to the information processing apparatus 5 having transmitted the request information.

In the embodiment, the server 4 is assumed to transmit the activity information during a period indicating the acquisition period information received from the information processing apparatus 5 to the information processing apparatus 5. However, the invention is not limited thereto. Ina case in which the acquisition period information is not included, the server 4 may be configured to transmit all of the activity information stored in association with the identification information included in the request information requesting the activity information to the information processing apparatus 5.

Configuration of Information Processing Apparatus

Figure 7:
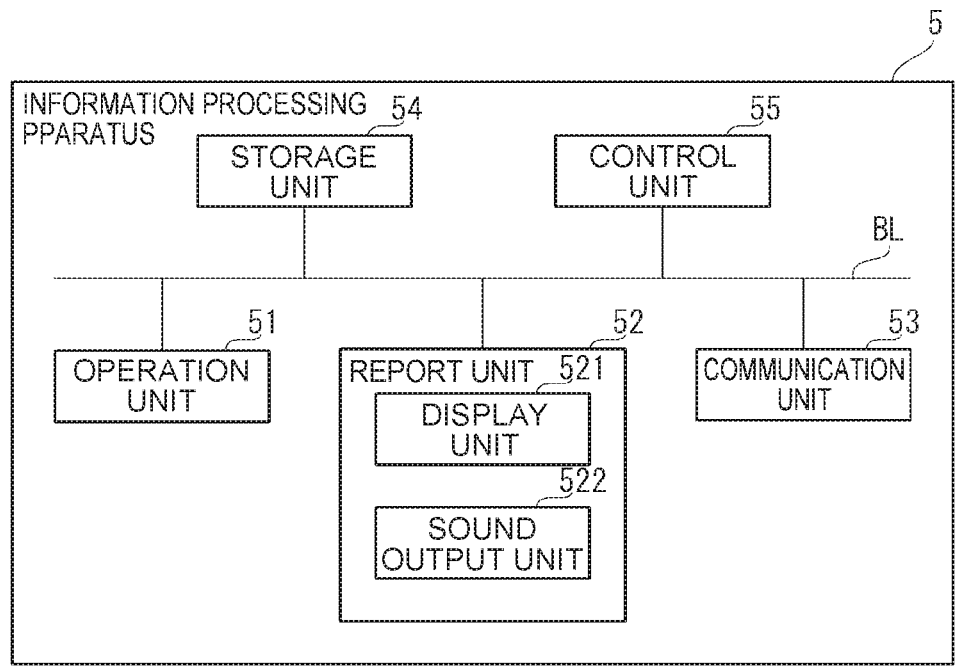
FIG. 7 is a block diagram illustrating the configuration of an information processing apparatus according to the embodiment.

FIG. 7 is a block diagram illustrating the configuration of the information processing apparatus 5.

The information processing apparatus 5 is included in the exercise content setting apparatus according to the invention, corresponds to a result information generation apparatus and an additional exercise setting apparatus according to the invention, and is configured to include, for example, a PC disposed in the facility FC. The information processing apparatus 5 authenticates a user entering the facility FC based on the identification information of the measurement apparatus 2 used by the user. Additionally, the information processing apparatus 5 presents an exercise menu indicating exercise content appropriate for a daily activity state of the user based on the activity information of the user stored in the server 4 and a purpose of the user.

As illustrated in FIG. 7, the information processing apparatus 5 includes an operation unit 51, a report unit 52, a communication unit 53, a storage unit 54, and a control unit 55. These units are connected to each other via a bus line BL.

Configuration of Operation Unit

The operation unit 51 receives an input operation of an operator (a user, a trainer and an instructor who coach the user, and a manager of the information processing apparatus 5) and outputs an operation signal according to the input operation to the control unit 35, as in the operation units 21 and 31. The operation unit 31 can be configured to include, for example, pointing devices such as a touch panel, a keyboard, and a mouse.

Configuration of Report Unit

The report unit 52 reports various kinds of information to the operator under the control of the control unit 55. The report unit 52 includes a display unit 521 and a sound output unit 522 as in the report unit 32.

The display unit 521 is configured to include any of various displays such as a liquid crystal display and an organic EL display and displays a predetermined image under the control of the control unit 55 to be described below. Examples of the image include an image indicating exercise content information that includes an exercise menu generated by the control unit 55 to be described below, an exercise result screen ES (see FIG. 12) to be described below and a task presentation screen CS (see FIG. 13) to be described below.

The sound output unit 522 is configured to include a sound output unit such as a speaker and outputs a sound according to sound information input from the control unit 55.

Configuration of Communication Unit

The communication unit 53 includes a communication module capable of communicating with the measurement apparatus 2, the processing terminal 3, and the server 4 under the control of the control unit 55. Here, in a case in which the communication unit 53 communicates with the apparatuses 2 to 4 in conformity to the same communication scheme, the communication unit 53 includes one communication module. Conversely, in a case in which communication schemes at the time of communication with these apparatuses are different, the communication unit 53 includes a plurality of communication modules according to the communication schemes.

The communication unit 53 communicates with the measurement apparatus 2 based on the connection information and acquires the identification information from the measurement apparatus 2 or the processing terminal 3, and also transmits exercise content information or the like set according to the user to the measurement apparatus 2 or the processing terminal 3.

Based on the acquired identification information, the communication unit 53 acquires the activity information stored in association with the identification information from the server 4.

Configuration of Storage Unit

The storage unit 54 is configured to include an HDD, an SSD, and a flash memory and stores various programs and data necessary for an operation of the information processing apparatus 5.

The storage unit 54 stores, for example, various programs such as an operating system (OS) and applications as the program. The program includes an exercise content setting application (including an exercise content setting program according to the invention) that executes an exercise content setting process of setting and presenting exercise content appropriate for the user. The exercise content setting process will be described in detail below.

The storage unit 54 stores connection information for communication connection with the measurement apparatus 2, the processing terminal 3, and the server 4 as the data. As the connection information, pairing information or an IP address can be exemplified. Further, the storage unit 54 stores the activity information acquired from the server 4 via the communication unit 53 at the time of execution of the exercise content setting process. Additionally, in a case in which the measurement apparatus 2 and the processing terminal 3 located in the facility FC transmit the activity information to the information processing apparatus 5, the storage unit 54 stores the activity information.

FIG. 8 is a diagram illustrating content of a user table TB1.

The storage unit 54 stores a user table TB1 in which personal information of a user to whom the measurement apparatus 2 is lent is registered. In the user table TB1, as illustrated in FIG. 8, personal information such as a name of the user, a date of birth, an age, a sex, a height, a weight, a use purpose of facility, favorite equipment, and dislike equipment is registered in association with the identification information of the measurement apparatus 2 lent to the user. The personal information is registered by operating the operation unit 51 by one of the user, an instructor, and a manager, for example, when the user uses (enters) the facility FC for the first time.

The use purpose of the facility also includes "record update" as well as "diet" and "improvement in physical strength" illustrated in FIG. 8. As the "record update", time update of long-distance running is exemplified.

The personal information may include presence or absence of exercise habits or a tendency of eating habits and sleep habits or may include a membership validity period or a goal achievement period. Although not illustrated, the personal information includes the number of visits to the facility FC or previous entrance dates and exit dates.

Additionally, data (facility use information) regarding facility use of the user such as the user table TB1 illustrated in FIG. 8 may be stored in the storage unit 54 of the information processing apparatus 5, and may also be stored in an information accumulation apparatus other than the storage unit 54 and may be acquired from the information accumulation apparatus based on the acquired identification information by the information processing apparatus 5. As the information accumulation apparatus, the server 4 or a data server different from the server 4 can be exemplified.

FIG. 9 is a diagram illustrating content of a use situation table TB2. In FIG. 9, a use situation of equipment from 13:00 to 16:00 on October 8 during a available time period of the equipment is extracted and indicated.

Further, the storage unit 54 stores the use situation table TB2 as use information in which a use situation of equipment disposed in the facility FC in which the information processing apparatus 5 is disposed is registered. In the use situation table TB2, as illustrated in FIG. 9, an hourly use frame (intervals of 15 minutes in the example of FIG. 9) of each predetermined time is set for each equipment name disposed in the facility FC in business hours of the facility FC. When a user of the facility FC (including the foregoing user) uses certain equipment in a certain time period, the identification information of the measurement apparatus 2 lent to the user, that is, identification information assigned to the user, is set in the equipment and the use frame according to the time period.

For example, in a case in which a user to whom identification information A07 is assigned uses equipment called bench press B from 15:00 to 15:30, the identification information A07 is registered in the use frame of bench press B from 15:00 to 15:30. In this way, use of the equipment is reserved.

Such use reservation of equipment may be individually made by each user or may be automatically made when each user approves of an exercise menu presented by the information processing apparatus 5 performing an exercise content setting process to be described below.

Although not illustrated, the storage unit 54 stores an assumption exercise intensity table, in which an exercise intensity (assumption exercise intensity) assumed at the time of arriving of the user to use the equipment is set, for each equipment.

Here, for example, in a treadmill, a load level applied to the user can be increased by adjusting an inclination of a step ladder. Therefore, in the assumption exercise intensity table, an assumption exercise intensity is set for each load level in regard to the equipment of which a load level can be adjusted.

The assumption exercise intensity table is referred to when the information processing apparatus 5 (specifically, the control unit 55) performs the exercise content setting process.

Configuration of Control Unit

Figure 10:
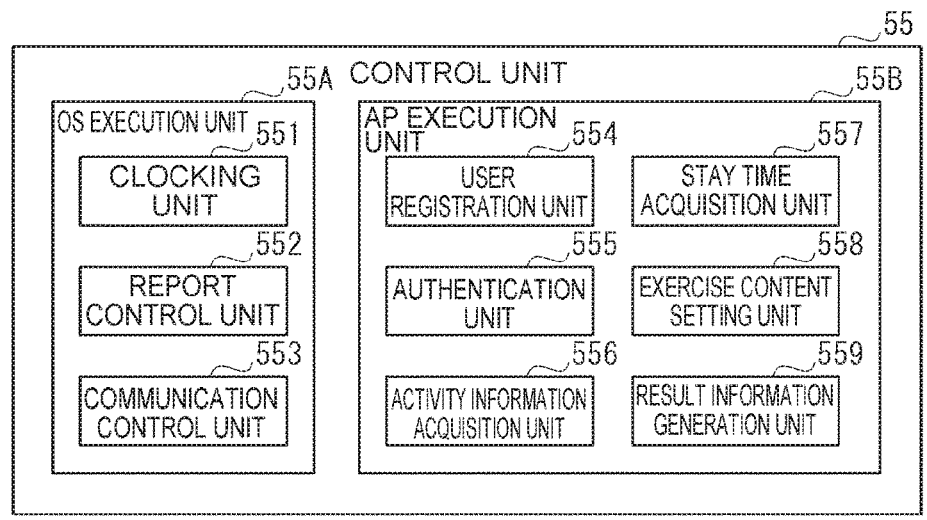
FIG. 10 is a block diagram illustrating the configuration of a control unit of the information processing apparatus according to the embodiment.

FIG. 10 is a block diagram illustrating the configuration of the control unit 55.

The control unit 55 illustrated in FIG. 7 includes an arithmetic processing circuit such as a CPU and controls an operation of the information processing apparatus 5 autonomously or according to an operation signal input from the operation unit 51 according to an operation of the user by executing a program stored in the storage unit 54 by the arithmetic processing circuit, as in the control units 28, 35, and 43.

The control unit 55 includes an OS execution unit 55A and an AP execution unit 55B, as illustrated in FIG. 10.

Configuration of OS Execution Unit

Figure 11:
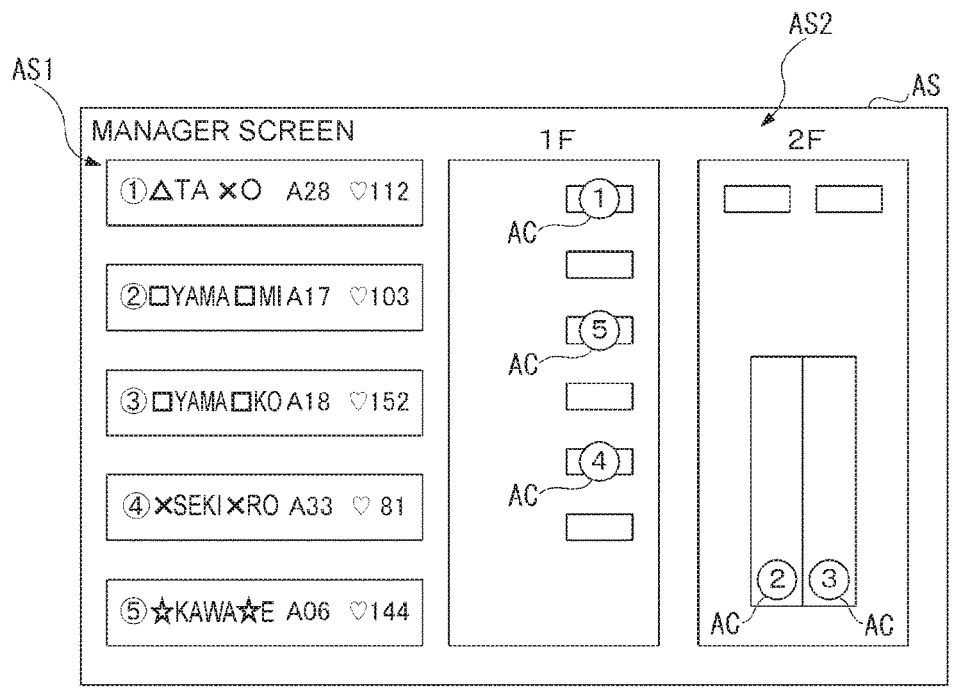
FIG. 11 is a diagram illustrating an example of a manager screen according to the embodiment.

FIG. 11 is a diagram illustrating an example of a manager screen AS displayed on the display unit 521.

The OS execution unit 55A is an functional unit that executes the OS stored in the storage unit 54 and includes a clocking unit 551, a report control unit 552, and a communication control unit 553.

The clocking unit 551 clocks a current date.

The report control unit 552 includes a display control unit and a sound output control unit, although not illustrated.

Of these units, the display control unit draws an execution-time screen of the program and displays the execution-time screen on the display unit 521. For example, as illustrated in FIG. 11, the display control unit displays the manager screen AS, which includes information indicating the name of the user entering the facility FC, the identification information, the pulse rate, and a current position of the user, on the display unit 521.

Not only a user display field AS1 in which the name of the user currently entering the facility FC, the identification information, and the pulse rate are set but also a layout AS2 of the facility FC are set in the manager screen AS. An icon AC indicating the position of each user is set in the layout AS2. The manager or the instructor of the information processing apparatus 5 can confirm the exercise state of each user and the position of the user in the facility FC by confirming such a manager screen AS. In a case in which the pulse rate is not shown in the manger screen AS, the measurement apparatus 2 or the processing terminal 3 may not continue transmitting the activity information to the server 4 or the information processing apparatus 5, or the position of each user in the layout AS2 may be specified in accordance with any of various methods.

The sound output control unit outputs a sound signal generated at the time of execution of the program and outputs a sound according to the sound signal to the sound output unit 522.

The communication control unit 553 controls communication of the communication unit 53 with an external apparatus.

Configuration of AP Execution Unit

As illustrated in FIG. 10, the AP execution unit 55B executes an application instructed by the OS execution unit 55A according to an operation signal input from the operation unit 51 among the applications stored in the storage unit 54. The AP execution unit 55B includes a user registration unit 554, an authentication unit 555, an activity information acquisition unit 556, a stay time acquisition unit 557, an exercise content setting unit 558, and a result information generation unit 559 which function when the CPU of the control unit 55 executes the exercise content setting application causing the AP execution unit 55B to perform the exercise content setting process.

Configuration of User Registration Unit

The user registration unit 554 acquires personal information of the user input with the operation unit 51 and registers the personal information in the user table TB1. Accordingly, the personal information is registered in membership registration of the user.

Configuration of Authentication Unit

The authentication unit 555 determines whether a person entering the facility FC is the user registered as a member and specifies the user in a case in which the authentication unit 555 determines that the person is the user registered as the member.

Specifically, in the embodiment, the measurement apparatus 2 is lent to the user registered as a member. The authentication unit 555 communicates with the measurement apparatus 2 mounted on the user entering the facility FC via the communication unit 53 and transmits the request information requesting the identification information to the communication unit 53. Thereafter, the authentication unit 555 determines whether the identification information transmitted in response to the request information and received by the communication unit 53 is registered in the user table TB1. When the authentication unit 555 determines that the identification information is not registered in the user table TB1, the authentication unit 555 determines that the user authentication is failed. Conversely, when the authentication unit 555 determines that the identification information is registered in the user table TB1, the authentication unit 555 determines that the user authentication is successful and specifies the user.

When the authentication unit 555 determines that the user authentication is successful, the activity information acquisition unit 556, the stay time acquisition unit 557, the exercise content setting unit 558, and the result information generation unit 559 are validated for the user on whom the measurement apparatus 2 having the authenticated identification information is mounted and the activity information of the user.

Hereinafter, the authenticated identification information is referred to as certified identification information in some cases. The user on whom the measurement apparatus 2 having the certified identification information is mounted is referred to as a certified user in some cases.

The authentication process by the authentication unit 555 may be automatically performed when the measurement apparatus 2 enters within a communication range by the communication unit 53 or may be performed when the user performs a predetermined operation on the operation unit 51. In this case, for example, when the communication unit 53 or the operation unit 51 is disposed at a dedicated member entrance of the facility FC, only the user registered as the member can enter the facility FC.

Configurations of Activity Information Acquisition Unit and Stay Time Acquisition Unit The activity information acquisition unit 556 acquires activity information accumulated in the server 4 in associated with the certified identification information from the server 4. Specifically, the activity information acquisition unit 556 transmits request information including the certified identification information to the server 4 through the communication unit 53 and acquires the activity information transmitted in response to the request information through the communication unit 53. In the embodiment, the request information transmitted by the activity information acquisition unit 556 includes the acquisition period information indicating a period in which the activity information is acquired. As the acquisition period, a period (period until a current date) from previous exit of the certified user from the facility FC to current entrance or a predetermined period (for example, for 1 month) until current entrance may be set. The previous exit date of the certified user can be stored in the user table TB1, as described above.

The stay time acquisition unit 557 acquires a scheduled stay time in the facility FC input with the operation unit 51 by the certified user.

Configuration of Exercise Content Setting Unit

The exercise content setting unit 558 sets content of an exercise to be performed by the certified user in the facility FC based on the personal information of the certified user and the acquired activity information and transmits exercise content information indicating the set content of the exercise to at least one of the measurement apparatus 2 and the processing terminal 3 used by the certified user.

As described in detail, the exercise content setting unit 558 first sets an exercise intensity (recommended exercise intensity) and an exercise time (recommended exercise time) of the exercise to be performed in the facility FC as the content of the exercise appropriate for a purpose included in the personal information.

The exercise content setting unit 558 sets an adjustment coefficient based on whether an exercise time after exit between the within-range exercise time (a within-range exercise time after exit) and the exercise time (the exercise time after exit) included in the activity information of the certified user and taken from the previous exit from the facility FC to the current entrance exceeds a first comparative value set based on the personal information such as the age, the sex, and the weight of the certified user and whether the within-range exercise time after exit exceeds a second comparative value set based on the personal information. The adjustment coefficient is a coefficient for further adjusting the set recommended exercise intensity and recommended exercise time and includes an intensity adjustment coefficient which is multiplied to the exercise intensity and a time adjustment coefficient which is multiplied to the exercise time.

The first and second comparative values are adjusted according to a period from the time of the previous exit of the certified user from the facility FC (the time of a previous exit operation) to the time of the current entrance (the time of a current entrance operation). For example, the first and second comparative values are adjusted to small values in a case in which the period is short. The first and second comparative values are adjusted to large values in a case in which the period is long. The same applies to a case in which activity information acquired by the activity information acquisition unit 556 is activity information during a predetermined period until the current entrance.

For example, in a case in which the exercise time after exit exceeds the first comparative value and the within-range exercise time after exit exceeds the second comparative value, the exercise content setting unit 558 determines that there is no problem in the daily exercise state of the certified user and sets a lowest value (for example, 1 respectively) in the intensity adjustment coefficient and the time adjustment coefficient.

In a case in which the exercise time after exit exceeds the first comparative value and the within-range exercise time after exit does not exceed the second comparative value, the exercise content setting unit 558 determines that a load is insufficient in the daily exercise state of the certified user and sets the smallest value in the time adjustment coefficient and sets a larger value (for example, 1.5) than the lowest value in the intensity adjustment coefficient.

Conversely, in a case in which the exercise time after exit does not exceed the first comparative value and the within-range exercise time after exit exceeds the second comparative value, the exercise content setting unit 558 determines that the load is sufficient in the daily exercise state of the certified user and determines that the certified user is not accustomed to exercise, and thus sets the lowest value in the intensity adjustment coefficient and sets the higher value (for example, 1.5) than the lowest value in the time adjustment coefficient.

On the other hand, in a case in which the exercise time after exit does not exceed the first comparative value and the within-range exercise time after exit does not exceed the second comparative value either, the exercise content setting unit 558 determines that neither the load nor the time is sufficient in the daily exercise state of the certified user and sets a highest value (for example, 2 respectively) in the intensity adjustment coefficient and the time adjustment coefficient.

The intensity adjustment coefficient set in this way is multiplied to the recommended exercise intensity and the time adjustment coefficient is multiplied to the recommended exercise time.

Further, the exercise content setting unit 558 further adjusts the recommended exercise intensity and the recommended exercise time based on the scheduled stay time which is acquired by the stay time acquisition unit 557 and in which the user stays in the facility FC.

For example, in a case in which the scheduled stay time is shorter than the recommended exercise time, the exercise content setting unit 558 increases or decreases the recommended exercise intensity based on a ratio of the recommended exercise time to the scheduled stay time and replaces the recommended exercise time with the scheduled stay time. Accordingly, the recommended exercise intensity of the exercise to be performed within the time in which the certified user stays in the facility FC, that is, the recommended exercise intensity appropriate for the purpose of the certified user and the daily exercise state (activity state) can be set.

In a case in which the scheduled stay time is not input by the user, the recommended exercise time is not replaced.

The exercise content setting unit 558 sets an exercise menu (training menu) according to the set recommended exercise intensity and recommended exercise time. At this time, the exercise content setting unit 558 sets the exercise menu satisfying the recommended exercise intensity and the recommended exercise time according to the personal information such as the sex, the age, and the weight, and the like of the certified user with reference to the assumption exercise intensity table. Such an exercise menu includes information indicating which exercise has to be performed, how much time the exercise has to be performed, and which equipment the user has to use. The exercise menu includes content in which the certified user has to perform a walking for 30 minutes in a pool, a chest press for 15 minutes, a cross trainer for 15 minutes. The exercise content setting unit 558 may set such a plurality of exercise menus.

When the exercise menu is set in this way, the exercise content setting unit 558 sets an equipment use order in which occurrence of a waiting time is most suppressed in use of the equipment included in the exercise menu with reference to the use situation table. For example, in a case in which a pool is not usable for 30 minutes due to use of other users and a chest press and a cross trainer are usable in the example of the exercise menu, the exercise content setting unit 558 sets the equipment use order in which the usable chest press and cross trainer are first used and the subsequently usable pool is used. When the exercise content setting unit 558 sets the equipment use order, the certified user can use each equipment indicated by the set exercise menu for a short waiting time.

In a case in which the plurality of exercise menus are set, the exercise menu in which the waiting time is the shortest and the favorite equipment of the user is preferred may be selected from the exercise menus and the equipment use order of the selected exercise menu may be set. When the user continues to perform the exercise, a large burden is considered to be imposed on the user and a change of clothes or the like is necessary in some cases. Therefore, when the exercise menu is planned, the exercise menu in which a predetermined rest time is ensured after the exercise performed by the user using one facility may be designed.

Such an exercise menu is transmitted to at least one of the measurement apparatus 2 and the processing terminal 3 of the certified user. When the exercise menu is approved through an input operation of the certified user on the apparatus, the exercise content setting unit 558 performs use registration of each equipment in the use situation table. Accordingly, the use registration of each equipment is completed without applying for the use registration of each equipment by the certified user.

In the embodiment, the exercise content setting unit 558 transmits the exercise content information to the measurement apparatus 2 mounted on the user so that the certified user does not perform the exercise while holding the processing terminal 3 when the certified user performs the exercise in the facility FC.

In the embodiment, the exercise content information includes not only the exercise menu but also the recommended exercise intensity and the recommended exercise time. However, as the exercise content information presented to the certified user, only the exercise menu may be presented or only the recommended exercise intensity and the recommended exercise time may be presented.

Configuration of Result Information Generation Unit

The result information generation unit 559 is a functional unit that has functions of an exercise result generation apparatus and the additional exercise setting apparatus according to the invention. As a result, in a case in which it is determined that the certified user performs an exit operation on the operation unit 51, the result information generation unit 559 generates exercise result information based on the activity information (the activation information in the facility) within a stay time in the facility FC and also generates a task (additional information) until the time of subsequent entrance. Then, the result information generation unit 559 generates the exercise result screen ES (see FIG. 12) including the exercise result information and the task presentation screen CS (see FIG. 13) including the task.

Configuration of Exercise Result Screen

Figure 12:
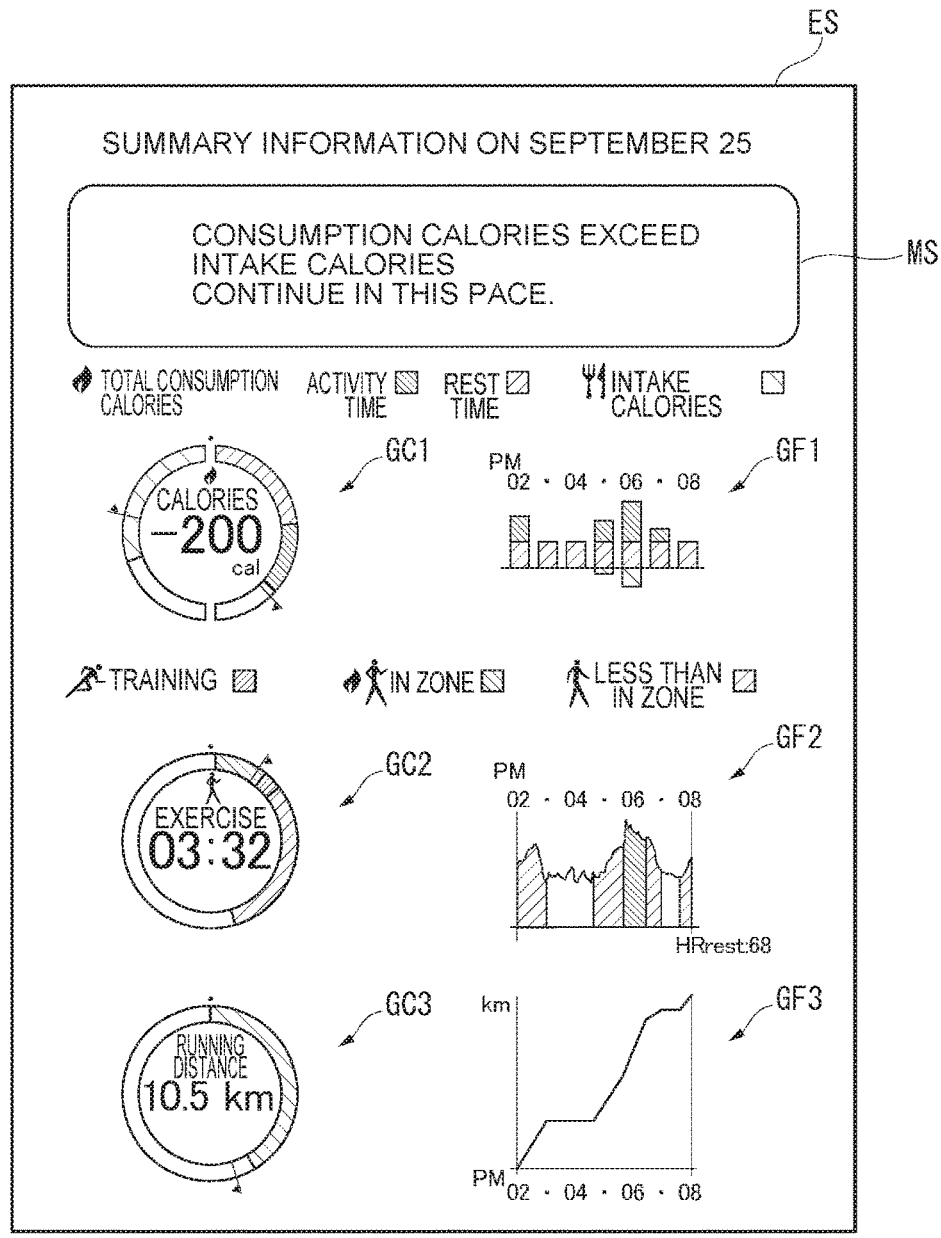
FIG. 12 is a diagram illustrating an example of an exercise result screen according to the embodiment.

FIG. 12 is a diagram illustrating an example of the exercise result screen ES.

The result information generation unit 559 acquires the activity information (the activation information in the facility) within the stay time of the certified user in the facility FC from the measurement apparatus 2, the processing terminal 3, or the server 4 and generates the exercise result information indicating the exercise result based on the activation information in the facility. The result information generation unit 559 generates the exercise result screen ES in which an example is illustrated in FIG. 12.

The exercise result screen ES includes exercise result information that includes: circular graphs GC1 to GC3 indicating a calorie balance, an exercise time, and a running distance based on the activity information in the facility of the certified user within a stay period (which is a period from execution of an entrance operation to execution of an exit process and is a period from 2:00 PM to 8:00 PM in the example of FIG. 12) in the facility FC and graphs GF1 to GF3 indicating transitions of the calorie balance, the pulse rate, and the running distance; and a message MS to the certified user based on the exercise result information. A graph indicating a transition of the exercise intensity may be set instead of or in addition to the graph GF2 indicating the transition of the pulse rate. Graphs or circular graphs indicating other information may be set instead of or in addition to the other graphs and circular graphs.

Here, the running distance is not a distance by the certified user actually running within the stay period but a value in a case in which an exercise amount practiced by the certified user within the stay period is converted into a running distance. Accordingly, even in a case in which another equipment is used on other entrance date of the facility FC, exercise amounts can be compared every entrance day. On the other hand, an exercise amount may not be replaced with a running distance, but may be replaced with another index.

An increase in the intake calories of the certified user within the stay period depends on intake of snack between meals eaten by the certified user within the stay period and registration of meal information regarding the snack between meals.

Configuration of Task Presentation Screen

Figure 13:
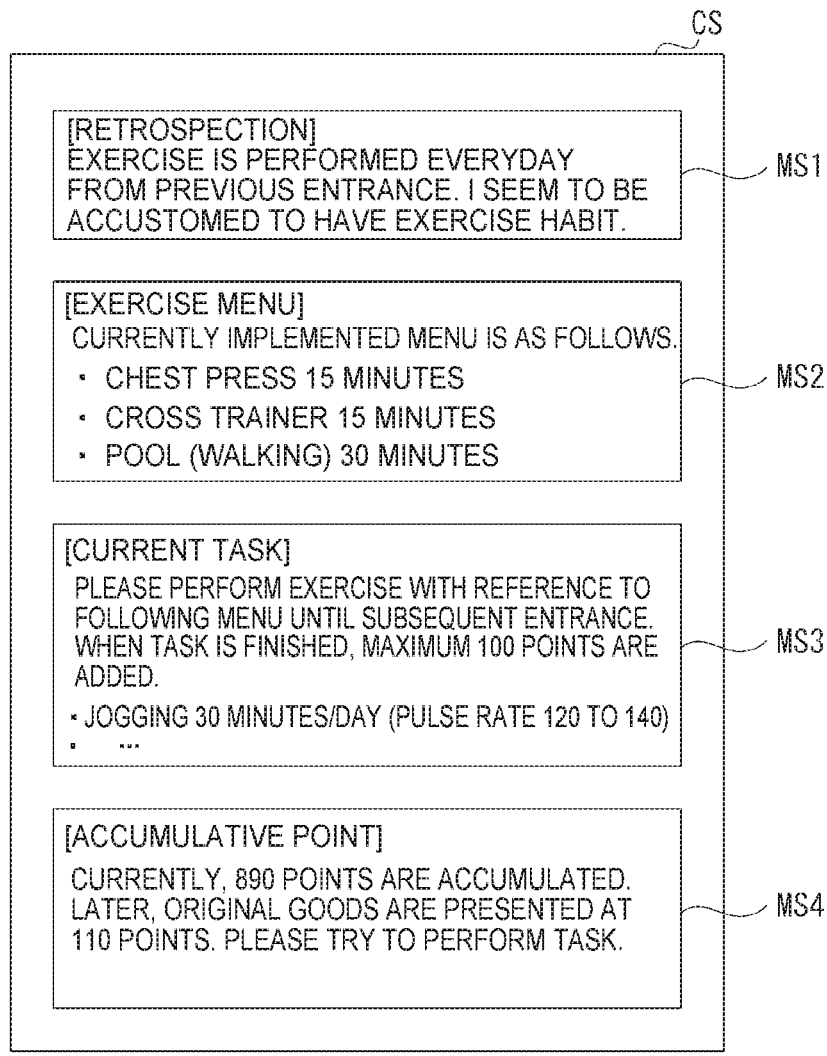
FIG. 13 is a diagram illustrating an example of a task presentation screen according to the embodiment.

FIG. 13 is a diagram illustrating an example of the task presentation screen CS.

The result information generation unit 559 generates a task to be performed by the certified user until subsequent entrance to the facility FC based on the activity information in the facility, and the activity information of a period from previous exit from the facility FC to current entrance or activity information (in particular, the exercise time and the within-range exercise time included in the activity information) in the predetermined period. Additionally, the result information generation unit 559 generates a determination result of exercise habit based on the activity information, an exercise menu implemented in the current facility FC, and a message for entrance privilege to the facility FC. The result information generation unit 559 generates the task presentation screen CS including the task and the message. At this time, the result information generation unit 559 calculates and grants points regarding the entrance privilege based on the activity information from the previous exit from the facility FC to the current entrance and the activity information in the current facility.

As illustrated in FIG. 13, the task presentation screen CS has four vertically arranged message display fields MS1 to MS4 in which a message regarding the determination result of the exercise habit, an exercise menu implemented by the user in the current facility FC, a task newly presented to the user, and a message for the entrance privilege are set, respectively.

The exercise result screen ES and the task presentation screen CS are displayed on the display unit 521 and are additionally transmitted to the measurement apparatus 2 and the processing terminal 3 of the certified user. Further, the screens ES and CS are printed by a printer and are delivered as print products to the certified user.

The exercise result screen ES and the task presentation screen CS may be one screen.

Exercise Content Setting Process by Information Processing Apparatus

Figure 14:
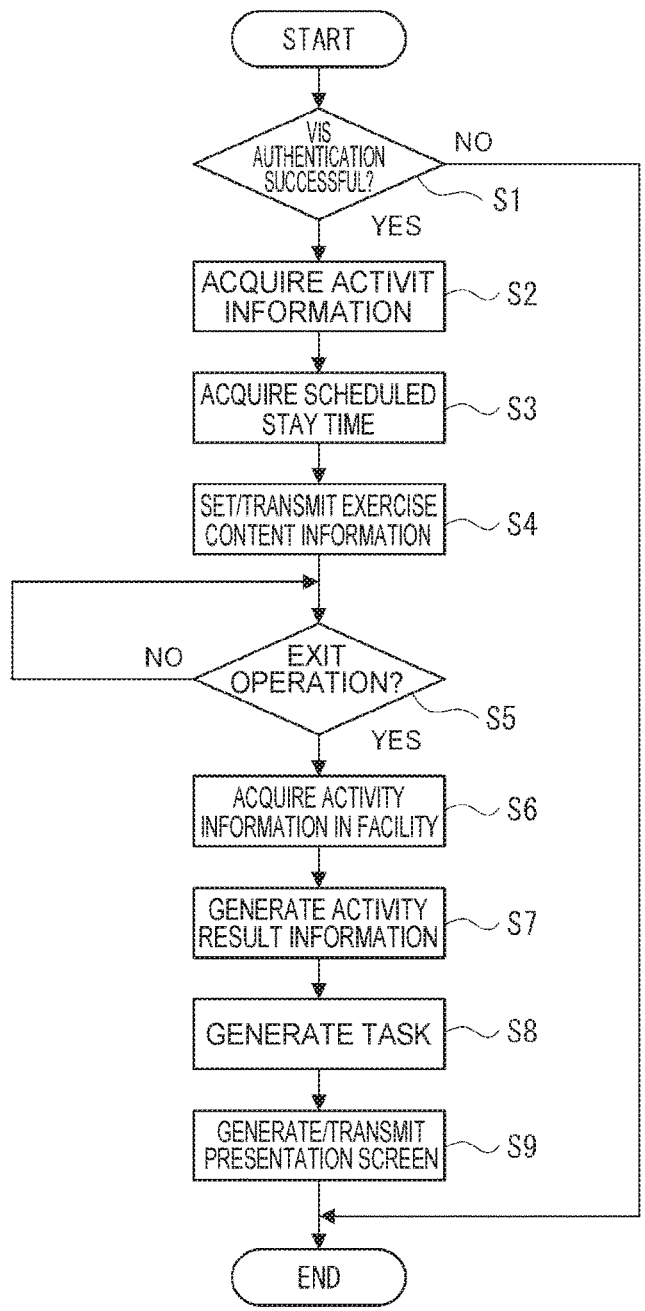
FIG. 14 is a flowchart illustrating an exercise content setting process according to the embodiment.

FIG. 14 is a flowchart illustrating the exercise content setting process performed by the control unit 55 of the information processing apparatus 5.

Hereinafter, the flow of the exercise content setting process performed by the information processing apparatus 5 will be described. The exercise content setting process is performed when an arithmetic processing device included in the control unit 55 executes the exercise content setting application stored in the storage unit 54, as described above.

Specifically, in the exercise content setting process, as illustrated in FIG. 14, the authentication unit 555 acquires the identification information of the measurement apparatus 2 mounted on the user entering the facility FC and determines whether the identification information is registered in the user table TB1 (step S1).

In a case in which authentication unit 555 determines that the acquired identification information is not registered in the user table TB1 in the determination process of step S1, the user authentication is determined to be failed and the control unit 55 ends the exercise content setting process.

Conversely, in a case in which the authentication unit 555 determines that the acquired identification information is registered in the user table TB1 in the determination process of step S1, the activity information acquisition unit 556 acquires the activity information stored in association with the identification information (step S2).

The stay time acquisition unit 557 acquires the scheduled stay time input by the certified user (step S3).

Then, the exercise content setting unit 558 generates and transmits the exercise content information including the recommended exercise intensity, the recommended exercise time, and the exercise menu additionally based on the acquired activity information and the scheduled stay time with reference to the personal information, the use situation table TB2, and the assumption exercise intensity table stored in association with the identification information in the user tale TB1 (step S4).

Thereafter, the result information generation unit 559 determines whether an exit operation is performed by the certified user (step S5). The determination process of step S5 is repeatedly performed until the exit operation is determined to be performed.

When the exit operation is determined to be performed by the certified user in the determination process of step S5, the result information generation unit 559 acquires the activity information in the facility based on the identification information associated with the certified user (step S6).

Then, the result information generation unit 559 generates the exercise result information and the task (steps S7 and S8), and further generates and transmits the exercise result screen ES and the task presentation screen CS (step S9).

Accordingly, the exercise content setting process ends.

In a case in which the activity information in the facility is periodically transmitted from the measurement apparatus 2 or the processing terminal 3, the process of step S6 may be repeatedly performed after step S4 and before step S5 until the exit operation is determined to be performed in step S5.

Advantages of Exercise Content Setting System

The exercise content setting system 1 according to the above-described embodiment has the following advantages.

Of the server 4 and the information processing apparatus 5 included in the exercise content setting apparatus, the server 4 communicates with at least one of the measurement apparatus 2 and the processing terminal 3 serving as the terminal apparatus acquiring and transmitting the daily activity information of the user and collects the daily activity information acquired from the apparatus. The information processing apparatus 5 sets the exercise content information indicating the content of the exercise according to the present purpose based on the activity information of the user collected and accumulated by the server 4. Thus, when the user (the user who can be authenticated by the authentication unit 555) enters the facility FC, the exercise content information appropriate for the preset purpose is set based on the daily activity information of the user. Thus, the user entering the facility FC can acquire and confirm the exercise content information without performing a predetermined exercise motion. Accordingly, it is possible to simply set and ascertain the exercise content appropriate for the purpose of the user.

When the activity information includes the analysis result information, the information processing apparatus 5 setting the exercise content information can appropriately ascertain the activity state such as the exercise state of the user during at least the period from the previous exit of the user from the facility FC to the current entrance to the facility FC. Accordingly, it is possible to simply and appropriately the exercise content information according to the activity state and the purpose of the user.

The information processing apparatus 5 transmits the set exercise content information to at least one of the measurement apparatus 2 and the processing terminal 3 used by the user. Thus, it is possible to confirm the exercise content information with one of the measurement apparatus 2 including the display unit 241 and the processing terminal 3 including the display unit 321. Accordingly, the user can easily ascertain the exercise content information.

In the embodiment, since the set exercise content information is transmitted to at least the measurement apparatus 2 mounted on the user, the user can easily confirm the exercise content information even in a case in which the user performs an exercise in the facility FC without carrying the processing terminal 3.

The information processing apparatus 5 is included in the same exercise content setting apparatus, acquires the activity information from the server 4 serving as the information accumulation apparatus that accumulates the daily activity information of the user from the measurement apparatus 2 or the processing terminal 3, and sets the exercise content information. Thus, the server 4 accumulates and retains the activity information, and thus it is possible to reduce the storage capacities of the storage unit 26 of the measurement apparatus 2 and the storage unit 34 of the processing terminal 3. Since the server 4 and the information processing apparatus 5 are separately configured, each processing load can be reduced and these apparatuses can also be disposed at mutually distant positions. Therefore, it is possible to improve the degree of disposition freedom.

The exercise content information set by the exercise content setting unit 558 includes not only the recommended exercise intensity and the recommended exercise time but also the exercise menu set based on the recommended exercise intensity and the recommended exercise time. Thus, the user can reliably perform the exercise appropriate for the purpose set by the user by performing the exercise based on the recommended exercise intensity and the recommended exercise time. Even the user who has no sufficient knowledge about the exercise intensity or the like can reliably and simply perform the exercise appropriate for the purpose by performing the exercise according to the exercise menu.

The storage unit 54 of the information processing apparatus 5 stores the use situation table TB2 as the use information indicating the use state of the equipment disposed in the facility FC. The exercise content setting unit 558 included in the control unit 55 of the information processing apparatus 5 sets the exercise menu in which the equipment for which the waiting time is the shortest is used when the user uses the equipment in the facility FC, based on the use situation table TB2. Thus, when the user enters the facility FC and performs the exercise according to the exercise menu, the user can perform the exercise efficiently in a short waiting time and can also utilize the equipment in the facility FC efficiently.

The result information generation unit 559 included in the control unit 55 of the information processing apparatus 5 generates the exercise result screen ES including the exercise result information indicating the result of the exercise performed by the user according to the exercise content information. Thus, the user can easily ascertain the content of the exercise performed by the user by confirming the exercise result screen ES. Accordingly, it is possible to further improve a motivation of the exercise.

The result information generation unit 559 generates the task presentation screen CS including the task (additional information) indicating the content of the exercise to be performed by the user outside the facility FC according to the purpose based on the activity information in the facility which is the result of the exercise performed by the user in the facility FC according to the exercise content information. Thus, since not only the content of the exercise to be performed by the user in the facility FC but also the content of the exercise to be performed outside the facility FC are presented, the user can be easily accustomed to have the exercise habit. Further, the user can efficiently perform the exercise appropriate for the purpose not only in the facility FC but also outside the facility FC when the user performs the exercise according to the task.

The exercise content setting unit 558 sets the exercise menu according to the scheduled stay time of the user in the facility FC. Thus, even the user whose scheduled stay time is short can efficiently perform the exercise appropriate for the purpose.

The measurement apparatus 2 retains the unique identification information and the authentication unit 555 of the information processing apparatus 5 authenticates and specifies the user based on the identification information acquired from the measurement apparatus 2 with reference to the user table TB1. Thus, the measurement apparatus 2 can be used instead of the membership card of the facility FC such as a training gym. Accordingly, it is possible to improve versatility and convenience of the measurement apparatus 2.

Here, in a case in which the purpose is, for example, a diet or an improvement in the body strength and a case in which an implementation time of the exercise is relatively short within an exercise intensity range in which fat burning or muscle strengthening is efficiently performed, it is hard to say that the exercise appropriate for the purpose is sufficiently performed although the daily exercise time is relatively long.

On the other hand, the exercise content setting unit 558 sets the intensity adjustment coefficient and the time adjustment coefficient based on the exercise time (specifically, the exercise time after exit) within a predetermined period in a daily life of the user included in the acquired activity information and the within-range exercise time (specifically, the within-range exercise time after exit) which is a time in which the exercise is performed within a predetermined exercise intensity range of the exercise time. The recommended exercise intensity and the recommended exercise time are adjusted based on the adjustment coefficients, and the exercise menu is set based on the recommended exercise intensity and the recommended exercise time. Thus, since the exercise content information is set in consideration of the daily exercise time and the within-range exercise time of the user, the load of the exercise to be performed by the user can be adjusted, for example, in a case in which the exercise appropriate for the purpose is not sufficiently performed or a case in which the physical and mental states are determined to be in a fatigue state due to a considerably large load. Accordingly, it is possible to perform the exercise appropriate for the user state.

Modifications of Embodiment

The invention is not limited to the foregoing embodiment, but modifications, improvements, or the like within the range in which the advantages of the invention can be achieved are included in the invention.

In the foregoing embodiment, the measurement apparatus 2 and the processing terminal 3 have been described as the terminal apparatuses according to the invention. However, the invention is not limited thereto. That is, when the measurement apparatus 2 can transmit the activity information to the server 4, the processing terminal 3 may not necessarily be provided.

On the other hand, the processing terminal 3 can utilize the display unit 321 relatively larger than the measurement apparatus 2 mounted on the user. Therefore, in a case in which the exercise content information or the exercise result screen ES and the task presentation screen CS are displayed so that the user can ascertain the exercise content information or the exercise result screen ES and the task presentation screen CS, it is preferably to use the processing terminal 3.

In the foregoing embodiment, the exercise content setting apparatus according to the invention has been configured, and the server 4 serving as the information accumulation apparatus and the information processing apparatus 5 have been configured to be separated. However, the invention is not limited thereto. That is, the information processing apparatus 5 and the information accumulation apparatus may be integrated. In this case, when the storage unit 54 of the information processing apparatus 5 is used as the information accumulation apparatus, the measurement apparatus 2 and the processing terminal 3 may transmit the activity information of the user to the information processing apparatus 5. In this case, the information processing apparatus 5 corresponds to the exercise content setting apparatus according to the invention.

In the foregoing embodiment, the exercise content setting unit 558 has set the recommended exercise intensity and the recommended exercise time, and the exercise content information including the exercise menu set based on the recommended exercise intensity and the recommended exercise time. However, the invention is not limited thereto. That is, the exercise content information including either the recommended exercise intensity and the recommended exercise time or the exercise menu may be generated. For example, the exercise content information including a recommended pulse rate or a recommended pace and an exercise time may be generated. That is, the information included in the exercise content information may be another information.

In the foregoing embodiment, the exercise content setting unit 558 has set the exercise content information based on the scheduled stay time in which the user is scheduled to stay in the facility FC. However, the invention is not limited thereto. That is, the exercise content information may be set without reference to the scheduled stay time and the exercise content information may be set based on another information.

The purpose of the user (that is, the use purpose of the facility by the user), that is, the purpose of the exercise, may be input by the user when the exercise content information is set and generated. In this case, the user can perform an exercise appropriate for each of different purposes.

In the foregoing embodiment, the information processing apparatus 5 has retained the use situation table TB2 and the exercise content setting unit 558 has set the exercise menu in which the user order of the equipment usable in a shortest waiting time is set with reference to the use situation table TB2. However, the invention is not limited thereto. That is, the information processing apparatus 5 may not retain the use situation table TB2 and such a setting method may not be performed by the exercise content setting unit 558. When the waiting time can be shortened in the exercise menu for which the longest waiting time is necessary, the waiting time may not be shortest. Further, the exercise content setting unit 558 may generate a plurality of exercise menus with reference to the use situation table TB2 and the control unit 55 of the information processing apparatus 5 may cause the report unit 52 to display the plurality of exercise menus. Then, the control unit 55 may be configured to decide one exercise menu among the plurality of exercise menus based on an operation signal input from the operation unit 51 as an exercise menu to be currently performed by the user and transmit the exercise menu to the measurement apparatus 2 or the processing terminal 3. The control unit 55 may be configured to transmit the plurality of exercise menus generated by the exercise content setting unit 558 to the measurement apparatus 2 or the processing terminal 3, so that the exercise menus selected by the user can be acquired with the apparatus receiving the plurality of exercise menus and the exercise menu to be performed currently by the user can be decided.

In the foregoing embodiment, the result information generation unit 559 has generated the exercise result screen ES including the exercise result information and the task presentation screen CS including the task which is the additional information indicating the content of the exercise to be performed outside the facility FC. However, the invention is not limited thereto. That is, the result information generation unit 559 may generate only one of the exercise result information and the task or may generate neither the exercise result information nor the task.

The screens ES and CS have been displayed on the display unit 521 and have also been transmitted to at least one of the measurement apparatus 2 and the processing terminal 3. Further, the screens ES and CS have been printed to be delivered to the user (the certified user). However, the invention is not limited thereto. For example, the screens ES and CS may not to be displayed on the display unit 521 and transmitted to at least one of the measurement apparatus 2 and the processing terminal 3, or may be displayed only on the display unit 521 and transmitted to neither the measurement apparatus 2 nor the processing terminal 3. Further, the screens ES and CS may not necessarily be printed.

In the foregoing embodiment, the result information generation unit 559 generating the exercise result information and the task (the additional information) is included in the information processing apparatus 5. However, the invention is not limited thereto. That is, an apparatus that has the functions of the result information generation unit 559 and that is configured to be separated from the information processing apparatus 5 may be provided. At this time, an apparatus generating the exercise result information and an apparatus generating the task may be separately provided. Further, the server 4 may have some of the functions of the result information generation unit 559.

In the foregoing embodiment, the authentication unit 555 has authenticated and specified the user using the measurement apparatus 2 based on the unique identification information stored in the measurement apparatus 2. However, the invention is not limited thereto. That is, the user may be authenticated by another configuration such as the membership card or the like. That is, the information processing apparatus, furthermore, the exercise content setting apparatus, may acquire the activity information of the user in association with the user.

In the foregoing embodiment, the measurement apparatus 2 has been configured to be lent to the user when the user enters the facility FC. However, the invention is not limited thereto. For example, the measurement apparatus 2 owned by the user may be registered and the exercise content information may be set by the information processing apparatus 5 according to the activity information based on measurement information measured by the measurement apparatus 2. In this case, the user and unique information of the measurement apparatus 2 such as a manufacturing number may be linked and registered in the user table TB1, and thus the authentication information of the user in the personal information may be managed.

In the foregoing embodiment, the measurement apparatus 2 has transmitted the activity information to the server 4 and the information processing apparatus 5 directly or via the processing terminal 3. However, the invention is not limited thereto.

For example, the activity information in the facility (the activity information acquired by the measurement apparatus 2 while the user is performing the exercise in the facility) may be configured to be transmitted from the measurement apparatus 2 to the server 4 or the information processing apparatus 5 via a repeater. In this case, when a plurality of repeaters are disposed in the facility and the user is located in the facility, the activity information acquired by the measurement apparatus 2 may be configured to be able to be acquired in real time by the server 4 or the information processing apparatus 5. Since a progress situation of the exercise menu can be confirmed in real time with the information processing apparatus 5 located in the facility as in the pulse rate indicated in the manager screen AS, a situation of the user can be easily ascertained even when a director such as an instructor does not accompany the user.

When identification information of each of the plurality of repeaters is granted, the repeater communicating with the measurement apparatus 2 transmits the identification information of the measurement apparatus 2 and the identification information of the repeater to the information processing apparatus 5, and the information processing apparatus 5 retains equipment information such as disposition locations or kinds of the repeaters and the equipment in association with the identification information of the repeaters, the current position of the user can be easily ascertained with the information processing apparatus 5. Thus, for example, position precision of each user set in the manager screen AS can be improved. Additionally, when a problem or an abnormal state occurs in a certain user, a staff such as a director can easily handle the problem or the abnormal state based on the activity information acquired by the information processing apparatus 5.

While the user stays in the facility, the measurement apparatus 2 may be configured to continuously transmit the activity information to the information processing apparatus 5 rather than the server 4 via the repeater and accumulate the activity information, and the measurement apparatus 2 may be configured to transmit the activity information accumulated in the measurement apparatus 2 to the server 4 at a predetermined timing after the exit operation. Even in this case, since the information processing apparatus 5 acquires the activity information accumulated after the previous exit from the facility from the server 4 at a timing at which the entrance operation is performed, the activity information of the user can be retained and stored with each of the information processing apparatus 5 and the server 4.

Even in the foregoing example, while the user stays in the facility, the measurement apparatus 2 may not continuously transmit the activity information to the information processing apparatus 5, and the activity information accumulated in the measurement apparatus 2 may be transmitted to the information processing apparatus 5 at a timing at which the exit operation is performed.

As described above, the information processing apparatus 5 disposed in the facility may retain the configuration of the server 4. In this case, the measurement apparatus 2 and the processing terminal 3 transmit the activity information to the information processing apparatus 5, and the information processing apparatus 5 accumulates the activity information of the user, and thus the activity information of each user can be unitarily managed in the information processing apparatus 5.

Further, for example, while the user stays in the facility, the measurement apparatus 2 may not transmit the activity information to the server 4 and may transmit the activity information to the information processing apparatus 5, and the information processing apparatus 5 may transmit the activity information of the user in the facility to the server 4 at a timing at which the exit operation is performed or a time point after the timing.

Additionally, for example, the measurement apparatus 2 may transmit the activity information to the server 4 at a predetermined timing, may start transmitting the activity information to the information processing apparatus 5 at a timing (the time of user authentication) at which the entrance operation is performed on the information processing apparatus 5 at the time of entrance to the facility, and may stop transmitting the activity information to the information processing apparatus 5 at a timing at which the exit operation is performed. Further, in a case in which the measurement apparatus 2 transmits the activity information to the information processing apparatus 5, the measurement apparatus 2 or the information processing apparatus 5 may store a date in which the entrance operation is performed and the measurement apparatus 2 may transmit the activity information to the information processing apparatus 5 from a timing at which the entrance operation is performed to a timing at which the exit operation is performed, autonomously or based on request information from the information processing apparatus 5.

In the foregoing embodiment, the activity information has included the meal information, the identification information of the measurement apparatus 2, and the analysis result information including each piece of derivation information derived by analyzing various kinds of information (the biological information, the body motion information, and the positional information) acquired by the measurement apparatus 2. The analysis result information has be set as the information that includes the exercise time and the within-range exercise time of detection dates of the transition of each of the pulse rate and the pace and the transition of the acquired positional information, the transition of the exercise intensity in the exercise time and the within-range exercise time, and the date information indicating the acquisition dates of the biological information, the body motion information, and the positional information serving as the bases of the derivation information. Further, the analysis result information may include the derivation information such as the intake calories, the consumed calories, the calorie balance, the sleep index value regarding the quality and depth of sleep, the index value regarding the degree of fatigue, the running distance, and the number of steps. However, the invention is not limited thereto. For example, the activity information may not include information regarding all of the items. That is, the content of the activity information can be appropriately modified when the activity information is information by which at least one user state can be determined and ascertained among the exercise state, the consumed-calorie state, and the physical body state during a certain period at least until the current entrance to the facility FC.

In the foregoing embodiment, the control unit 55 has read and executed the exercise content setting application (including the exercise content setting program) stored in the storage unit 54. However, the invention is not limited thereto. For example, when the exercise content setting process is performed, the exercise content setting program may be read from a recording medium to be executed. For example, as the recording medium, a magnetic tape, a magnetic disk, an optical disc, a magneto-optical disc, a hard disk device, a semiconductor memory, or the like can be used. Not only can the exercise content setting program be installed and executed in the information processing apparatus using such a recording medium, but the exercise content setting program can also be distributed easily. Further, the exercise content setting program may be acquired from an apparatus on a network to be executed.

What is claimed is:

1. An exercise content setting system comprising:
   a terminal apparatus that acquires and transmits activity information of a user; and
   an exercise content setting apparatus associated with a predetermined facility and that sets exercise content information indicating an exercise content, which includes one or more exercises to be performed by the user, according to a preset purpose based on the activity information acquired from the terminal apparatus,
   wherein the activity information includes
      daily activity information that indicates activity of the user performed while the user is away from the predetermined facility, and
      facility activity information that indicates activity of the user performed while the user is at the predetermined facility, and
   the exercise content setting apparatus sets the exercise content information and the one or more exercises to be performed by the user, based on both the daily activity information and the facility activity information,
   the exercise content information includes at least one of an exercise intensity and an exercise time of the one or more exercises to be performed by the user and an exercise menu, which contains an order in which the one or more exercises should be performed, set based on the exercise intensity and the exercise time,
   the exercise content setting apparatus retains use information indicating a use state of equipment disposed in the predetermined facility, the use state indicates whether or not the equipment is scheduled to be in use by another user while exercises are being performed by the user, and
   in a case in which the exercise menu is included in the exercise content information, the order of exercises in the exercise menu is set such that a waiting time for the equipment is shortest based on the use state of the equipment in the predetermined facility.

2. The exercise content setting system according to claim 1,
   wherein the activity information includes at least one of an exercise intensity of an exercise performed by the user, an exercise time of the exercise, consumed calories of the user, a calorie balance which is a balance of intake calories and the consumed calories of the user, an index value regarding a sleep state of the user, and an index value regarding a degree of fatigue of the user.

3. The exercise content setting system according to claim 1,
   wherein the exercise content setting apparatus transmits the set exercise content information to the terminal apparatus.

4. The exercise content setting system according to claim 1,
   wherein the exercise content setting apparatus includes
   an information accumulation apparatus that accumulates the activity information, and
   an information processing apparatus that acquires the activity information from the information accumulation apparatus and sets the exercise content information based on the acquired activity information.

5. The exercise content setting system according to claim 1, further comprising:
   a result information generation apparatus that generates exercise result information indicating a result of the exercise performed by the user according to the exercise content information.

6. The exercise content setting system according to claim 1,
   wherein the exercise content indicated by the exercise content information includes an exercise to be performed by the user in the predetermined facility, and
   wherein the exercise content setting system further comprises:

an additional exercise content setting apparatus that sets additional exercise content information indicating additional exercise content to be performed by the user away from the predetermined facility according to the preset purpose based on a result of the exercise performed by the user according to the exercise content information.

7. The exercise content setting system according to claim 1,
wherein the exercise content indicated by the exercise content information includes an exercise to be performed by the user in the predetermined facility, and
wherein the exercise content setting apparatus sets the exercise content information according to a scheduled stay time of the user in the predetermined facility.

8. The exercise content setting system according to claim 1,
wherein the terminal apparatus retains unique identification information, and
wherein exercise content setting apparatus acquires the identification information and specifies the user based on the acquired identification information.

9. The exercise content setting system according to claim 1,
wherein the exercise content setting apparatus sets the exercise content information based on an exercise time of the user based on the activity information and a within-range exercise time which is a time in which the exercise is performed within a predetermined exercise intensity range in the exercise time.

10. The exercise content setting system according to claim 1, wherein
the exercise content setting apparatus registers points in time indicating whenever a user enters and exits the predetermined facility, and
when the exercise content setting apparatus acquires the activity information, only the daily activity information of the user that occurred from a most recent exit point in time to a most recent entrance point in time is acquired.

11. An exercise content setting apparatus comprising:
an activity information acquisition unit associated with a predetermined facility and that acquires activity information of a user from a terminal apparatus that acquires and transmits the activity information of the user; and
an exercise content setting unit that sets an exercise content information, which includes one or more exercises to be performed by the user, according to a preset purpose based on the acquired activity information,
wherein the activity information includes
daily activity information that indicates activity of the user performed while the user is away from the predetermined facility, and
facility activity information that indicates activity of the user performed while the user is at the predetermined facility, and
the exercise content setting unit sets the exercise content information and the one or more exercises to be performed by the user based on both the daily activity information and the facility activity information,
the exercise content information includes at least one of an exercise intensity and an exercise time of the one or more exercises to be performed by the user and an exercise menu, which contains an order in which the one or more exercises should be performed, set based on the exercise intensity and the exercise time,
the exercise content setting unit retains use information indicating a use state of equipment disposed in the predetermined facility, the use state indicates whether or not the equipment is scheduled to be in use by another user while exercises are being performed by the user, and
in a case in which the exercise menu is included in the exercise content information, the order of exercises in the exercise menu is set such that a waiting time for the equipment is shortest based on the use state of the equipment in the predetermined facility.

12. An exercise content setting method which is performed using an information processing apparatus associated with a predetermined facility and is a method of setting an exercise content performed by a user, the method comprising:
acquiring activity information of the user by the information processing apparatus;
setting an exercise content, which includes one or more exercises to be performed by the user, according to a preset purpose based on the acquired activity information by the information processing apparatus; and
acquiring use information indicating a use state of equipment disposed in the predetermined facility, the use state indicating whether or not the equipment is scheduled to be in use by another user while exercises are being performed by the user,
wherein the activity information includes
daily activity information that indicates activity of the user performed while the user is away from the predetermined facility, and
facility activity information that indicates activity of the user performed while the user is at the predetermined facility, and
the exercise content and the one or more exercises to be performed by the user are set based on both the daily activity information and the facility activity information,
the exercise content includes at least one of an exercise intensity and an exercise time of the one or more exercises to be performed by the user and an exercise menu, which contains an order in which the one or more exercises should be performed, set based on the exercise intensity and the exercise time,
in a case in which the exercise menu is included in the exercise content, the order of exercises in the exercise menu is set such that a waiting time for the equipment is shortest based on the use state of the equipment in the predetermined facility.

13. The exercise content setting method according to claim 12, further comprising:
generating exercise result information indicating a result of the exercise performed by the user according to the exercise content.

14. The exercise content setting method according to claim 12,
wherein the exercise content includes an exercise to be performed by the user in the predetermined facility, and
wherein the exercise content setting method further comprises:
setting additional exercise content to be performed by the user away from the predetermined facility according to the preset purpose based on a result of the exercise performed by the user according to the exercise content.

15. An exercise content setting program, stored in a non-transitory computer-readable storage medium, which is executed by an information processing apparatus associated with a predetermined facility and sets an exercise content, which includes one or more exercises to be performed by a user, the program causing the information processing apparatus to perform:

acquiring activity information of the user; and setting the exercise content according to a preset purpose based on the acquired activity information; and acquiring use information indicating a use state of equipment disposed in the predetermined facility, the use state indicating whether or not the equipment is scheduled to be in use by another user while exercises are being performed by the user, wherein the activity information includes daily activity information that indicates activity of the user performed while the user is away from the predetermined facility, and facility activity information that indicates activity of the user performed while the user is at the predetermined facility, and the exercise content and the one or more exercises to be performed by the user are set based on both the daily activity information and the facility activity information, the exercise content includes at least one of an exercise intensity and an exercise time of the one or more exercises to be performed by the user and an exercise menu, which contains an order in which the one or more exercises should be performed, set based on the exercise intensity and the exercise time, in a case in which the exercise menu is included in the exercise content, the order of exercises in the exercise menu is set such that a waiting time for the equipment is shortest based on the use state of the equipment in the predetermined facility.

16. The exercise content setting program according to claim 15, wherein the exercise content setting program causes the information processing apparatus to further perform:

generating exercise result information indicating a result of the exercise performed by the user according to the exercise content.

17. The exercise content setting program according to claim 15, wherein the exercise content includes an exercise to be performed by the user in the predetermined facility, and wherein the exercise content setting method further comprises:

setting additional exercise content to be performed by the user away from the predetermined facility according to the preset purpose based on a result of the exercise performed by the user according to the exercise content.

* * * * *